(12) United States Patent
Bai et al.

(10) Patent No.: US 8,338,155 B2
(45) Date of Patent: Dec. 25, 2012

(54) MODIFIED MEVALONATE KINASE WITH REDUCED FEEDBACK INHIBITION

(75) Inventors: Renyuan Bai, Baltimore, MD (US); Markus Wyss, Liestal (CH)

(73) Assignee: DSM IP Assets B.V., Heerlen (NL)

( * ) Notice: Subject to any disclaimer, the term of this patent is extended or adjusted under 35 U.S.C. 154(b) by 853 days.

(21) Appl. No.: 11/793,349

(22) PCT Filed: Dec. 12, 2005

(86) PCT No.: PCT/EP2005/013282
§ 371 (c)(1),
(2), (4) Date: Jul. 18, 2007

(87) PCT Pub. No.: WO2006/063752
PCT Pub. Date: Jun. 22, 2006

(65) Prior Publication Data
US 2007/0286850 A1    Dec. 13, 2007

(30) Foreign Application Priority Data
Dec. 14, 2004    (EP) ..................... 04029529

(51) Int. Cl.
*C12N 9/12* (2006.01)
(52) U.S. Cl. ....................................... 435/194
(58) Field of Classification Search ........................ None
See application file for complete search history.

(56) References Cited

U.S. PATENT DOCUMENTS

| | | |
|---|---|---|
| 6,242,227 B1 | 6/2001 | Millis et al. |
| 6,284,506 B1 | 9/2001 | Hoshino et al. |
| 6,410,755 B1 | 6/2002 | Millis et al. |
| 6,989,257 B2 | 1/2006 | Berry et al. |
| 7,422,884 B2 * | 9/2008 | Bai et al. ............... 435/194 |
| 2003/0125573 A1 | 7/2003 | Millis et al. |
| 2003/0148416 A1 | 8/2003 | Berry et al. |
| 2005/0266518 A1 | 12/2005 | Berry et al. |

FOREIGN PATENT DOCUMENTS

| | | |
|---|---|---|
| WO | 00/01649 | 1/2000 |
| WO | 02/099095 A2 | 12/2002 |
| WO | 2004/111214 A1 | 12/2004 |

OTHER PUBLICATIONS

Ferreira, International Search Report for PCT/EP2005/013282, five pages, mailed Mar. 31, 2006.
Houten et al., "Biochemical and genetic aspects of mevalonate kinase and its deficiency" Biochem. Biophys. Acta, vol. 1529, No. 1-3, pp. 19-32 (2000).
Hümelin et al., "Genetics of isoprenoid biosynthesis in *Paracoccus zeaxanthinifaciens*" Gene, vol. 297, No. 1-2, pp. 129-139 (2002).
Whisstock et al, "Prediction of protein function from protein sequence and structure", Quarterly Reviews of Biophysics 36, 3 (2003), pp. 307-340.
Gayle et al, "Identification of Regions in Interleukin-1α Important for Activity", The Journal of Biological Chemistry, vol. 268, No. 29, pp. 22105-22111, 1993.

* cited by examiner

*Primary Examiner* — David J Steadman
(74) *Attorney, Agent, or Firm* — Nixon & Vanderhye P.C.

(57) ABSTRACT

The present invention relates to modified mevalonate kinases that are less sensitive to feedback inhibition, and to polynucleotides encoding them. The invention further pertains to vectors comprising these polynucleotides and host cells containing such vectors. The invention provides a process for producing the modified enzyme and for producing isoprenoid compounds using the modified enzymes.

1 Claim, 3 Drawing Sheets

Figure 1.

```
Mvk_mouse                --MLSEALLVSAPGKVILHGEHAVVHGKVALAAALN-LRTFLLLRP----  43
Mvk_rat                  --MLSEVLLVSAPGKVILHGEHAVVHGKVALAVALN-LRTFLVLRP----  43
Mvk_H_sapiens            --MLSEVLLVSAPGKVILHGEHAVVHGKVALAVSLN-LRTFLRLQP----  43
Mvk_P_rhodozyma          ----KEEILVSAPGKVILFGEHAVGHGVTGIAASVD-LRCYALLSPTATT  45
Mvk_S_pombe              ---MSKSLIVSSPGKTILFGEHAVVYGATALAAAVS-LRSYCKLQT----  42
Mvk_A_pernix             ---MRRAARASAPGKVIIVGEHFVVRGSLAIVAAIG--------------  33
Mvk_P_abyssi             ---MPRLVLASAPAKIILFGEHSVVYGKPAIASAID-LRTYVRAEF----  42
Mvk_P_horikoshii         ---MVKYVLASAPAKVILFGEHSVVYGKPAIASAIE-LRTYVRAQF----  42
Mvk_P_furiosus           -----MKVIASAPAKVILFGEHSVVYGKPAIAAAID-LRTFVEAEL----  40
Mvk_M_thermoautotrophicum -----MKSSASAPAKAILFGEHAVVYSKPAIAAAID-RRVTVTVSE----  40
Mvk_A_fulgidus           --------MIASAPGKIILFGEHAVVYGRHAVVSAIN-LRCRVSVRK---  38
Mvk_M_jannaschii         --------MIIETPSKVILFGEHAVVYGYRAISMAIDLTSTIEIKETQ--  40
Mvk_P_zeaxanthinifaciens MSTGRPEAGAHAPGKLILSGEHSVLYGAPALAMAIARYTEVWFTPLG---  47
Mvk_yeast                ---MSLPFLTSAPGKVIIFGEHSAVYNKPAVAASVSALRTYLLISE----  43

Mvk_mouse                -----QSNGKVSVNLPNIGIKQVWDVGMLQR-LDTSFLE------QGDVS  81
Mvk_rat                  -----QSNGKVSLNLPNVGIKQVWDVATLQL-LDTGFLE------QGDVP  81
Mvk_H_sapiens            -----HSNGKVDLSLPNIGIKRAWDVARLQS-LDTSFLE------QGDSIPE  81
Mvk_P_rhodozyma          TTSSSLSSTNITISLTDLNFTQSWPVDSLPWSLAPDWTE------ASIPE  89
Mvk_S_pombe              ----TNN-NEIVIVMSDIGTERRWNLQSLPWQHVTVEN------VQHPAS  81
Mvk_A_pernix             --------RRLRVTVRSGGKGIVLESSMLGR-------------HSAP   60
Mvk_P_abyssi             --------NDSGNIKIEAHDIKTPGLIVSFSEDKIYFETD------YGKAA 79
Mvk_P_horikoshii         --------NDSGNIKIEAHDIKTPGLIVSFSEDKIYFETD------YGKAA 79
Mvk_P_furiosus           --------IREKKIRIEAHDIKVPGLTVSFSENEIYFETD------YGKAA 77
Mvk_M_thermoautotrophicum --------SSSTHVTIPSLGIRHS------SER-----------PSG   62
Mvk_A_fulgidus           --------SDR-------FLIRSS-----LGES------------GLDY   55
Mvk_M_jannaschii         --------EDEIILNLNDLNKSLGLNLNEIKN-----------INPNNF  70
Mvk_P_zeaxanthinifaciens ------IGEGIRTTFANLSGGATYSLKLLSGFKSRLDRR------FEQFL 85
Mvk_yeast                ----SSAPDTIELDFEDISINHKWSINDFNAITEDQVNSQKLAEAQQATD 89

Mvk_mouse                VPTLEQLEKLKKMGDLPRDRAGNEGMALLAFLYLYLAICRKQRTLPSLDM 131
Mvk_rat                  APTLEQLEKLKVAGLPRDCVGNEGLSLLAFLYLYLAICRKQRTLPSLDI 131
Mvk_H_sapiens            TPTSEQVEKLKEVAGLPDDCAVTERLAVLAFLYLYLSICRKQRALPSLDI 131
Mvk_P_rhodozyma          SLCPTLLAEIERIAGQGGNGGEREKVATMAFLYLLVLLSKGKPSEP-FEL 138
Mvk_S_pombe              SPNLDLLQGLGELLKNEENG--LIHSAMLCTLYLFTSLS---SPSQGCTL 126
Mvk_A_pernix             LPGQGAAAKVSPVLEP--------------YIAVLRSLAARGYSVVPHTI  96
Mvk_P_abyssi             EVLSYVRHAIELVLEEADKR--------------------TGVSV 104
Mvk_P_horikoshii         EVLSYVRYAIELALEESDKR--------------------VGIDV 104
Mvk_P_furiosus           EVLSYVREAINLVLEEADKKN-------------------VGIKV 103
Mvk_M_thermoautotrophicum GILDYIGRCLELYHDA--------------------SPLDI 83
Mvk_A_fulgidus           QRHPYVVQAVKRFGELRNIP-------------------GAEI 79
Mvk_M_jannaschii         GDFKYCLCAIKNTLDYLNIEP-----------------KTGFKI 97
Mvk_P_zeaxanthinifaciens NGDLKVHKVLTHPDDLAVYALASLLHDKPPGTAAMPGIGAMHHLPRPGEL 135
Mvk_yeast                GLSQELVSLLDPLLAQESES--FEYHAAFEFLYMFVCLC---PHAKNIKF 134

Mvk_mouse                VVWSELPPGAGLGSSAAYSVCLAAALLTACEEVSNPLKDGVSVSRWPEED 181
Mvk_rat                  MVWSELPPGAGLGSSAAYSVCVAAALLTACEEVTNPLKDRGSIGSWPEED 181
Mvk_H_sapiens            VVWSELPPGAGLGSSAAYSVCLAAALLTVCEEIPNPLKDGDCVNRWTKED 181
Mvk_P_rhodozyma          TARSALPMGAGLGSSAALSTSLALVFLLHFSHLSPTTTGRE--STIPTAD 186
Mvk_S_pombe              TISSQVPLGAGLGSSATISVVVATSLLLAFGNIEPPS---SNSLQNNKA 172
Mvk_A_pernix             LVESGIPPRAGLGSSAASMVAYALSYSAMHGDP---------------LS 131
Mvk_P_abyssi             SITSQIPVGAGLGSSAAVAVATIGAVSKLLDLELS-------------- 139
Mvk_P_horikoshii         SITSQIPVGAGLGSSAAVAVATIGAVSRLLGLELS-------------- 139
Mvk_P_furiosus           SITSQIPVGAGLGSSAAVAVATIGAVSKLLGLELS-------------- 138
Mvk_M_thermoautotrophicum RVEMEIPAGSGLGSSAALTVALIGALDRYHGRDHG----------- 118
Mvk_A_fulgidus           EIESEIPIGSGLGSSAAVIVATIAALNAEFDGDMD----------- 114
Mvk_M_jannaschii         NISSKIPISCGLGSSASITIGTIKAVSGFYNKELK----------- 132
Mvk_P_zeaxanthinifaciens GSRTELPIGAGMGSSAAIVAATTVLFETLLDRPKT----------- 170
Mvk_yeast                SLKSTLPEGAGLGSSASESSVSLAEAMAYLGGLIGSND----LEKLSEN-D 179

Mvk_mouse                LKSINKWAFEGERVIHGNPSGVDNAVSTWGGALRFQ--------QGTMS 222
Mvk_rat                  LKSINKWAYEGERVIHGNPSGVDNSVSTWGGALRYQ--------QGKMS 222
Mvk_H_sapiens            LELINKWAFQGERMIHGNPSGVDNAVSTWGGALRYH--------QGKIS 222
Mvk_P_rhodozyma          TEVIDKWAFLAEKVIHGNPSGIDNAVSTRGGAVAFKR--KIEGKQEGGME 234
```

Figure 1 (continued)

```
Mvk_S_pombe              LALIEAWSFLGECCIHGTPSGIDNAVATNGGLIAFRKATAHQSAMK---E 219
Mvk_A_pernix             AEDLYSVAMEGEKIAHGKPSGVDVTIAVRGGVLAYRR-------GENPVD 174
Mvk_P_abyssi             KEEIAKMGHKVELLVQGASSGIDPTVSAIGGFLYYK----------QGEF 179
Mvk_P_horikoshii         KEEIAKLGHKVELLVQGASSGIDPTVSAVGGFLYYK----------QGKF 179
Mvk_P_furiosus           KEEIAKMGHKTELLVQGASSGIDPTVSAIGGFIFYE----------KGKF 178
Mvk_M_thermoautotrophicum PGETAARAHRVEVDVQGAASPLDTAISTYGGLVYLDS---------QRRV 159
Mvk_A_fulgidus           KEAIFQMAKQVEIDVQGRASGIDPFISTFGGSWLFP----------ERRK 154
Mvk_M_jannaschii         DDEIAKLGYMVEKEIQGKASITDTSTITYKGILEIKN---NKFRKIKGEF 179
Mvk_P_zeaxanthinifaciens PEQRFDRVRFCERLKHGKAGPIDAASVVRGGLVRVGG-----------N 208
Mvk_yeast                KHIVNQWAFIGEKCIHGTPSGIDNAVATYGNALLFEKDSHNGTINTNNFK 229

Mvk_mouse                SLKSLPSLQILLTNTKVPRSTKALVAAVRSRL--TKFPEIVAPLLTSIDAI 271
Mvk_rat                  SLKRLPALQILLTNTKVPRSTKALVAGVRSRL--IKFPEIMAPLLTSIDAI 271
Mvk_H_sapiens            SLKRSPALQILLTNTKVPRNTKALVAGVRNRL--LKFPEIVAPLLTSIDAI 271
Mvk_P_rhodozyma          AIKSFTSIRFLITDSRIGRDTRSLVAGVNARL--IQEPEVIVPLLEAIQQI 283
Mvk_S_pombe              FLKPKDTLSVMITDTKQPKSTKKLVQGVFELK--ERLPTVIDSIIDAIDGI 268
Mvk_A_pernix             IRPGLTGVTLLVADTGVERRTRDVVEHVLSIA--DALGEASTYIYRAADLI 223
Mvk_P_abyssi             EHLPFVELPIVVGYTGSSGSTKELVAMVRRRY--EEMPELIEPILESMGKL 228
Mvk_P_horikoshii         EPLPFMELPIVVGYTGSTGSTKELVAMVRKRY--EEMPELVEPILEAMGKL 228
Mvk_P_furiosus           EHLPFMELPIVVGYTGSSGPTKELVAMVRKRY--EEMPELIVPILEAMGKV 227
Mvk_M_thermoautotrophicum RQFEADLGDLVIAHLDYSGETARMVAGVAERF--RRFPDIMGRIMDTVESI 208
Mvk_A_fulgidus           VEMPFKFFVINFG----SRSTAEMVAKVAELR--ERHPEVVDKIFDAIDAI 199
Mvk_M_jannaschii         EEFLKNCKFLIVYAEKRKKKTAELVNEVAKIE------NKDEIFKEIDKV 223
Mvk_P_zeaxanthinifaciens GPGSISSFDLPEDHDLVAGRGWYWVLHGRPVSGTGECVSAVAAAHGRDAA 258
Mvk_yeast                FSDDFPAIPMILTYTRIPRSTKDLVARVRVLVTEKFPEVMKPILDAMGEC 279

Mvk_mouse                SLECERVLG--EMVAAP-------VPEQYLVLEELIDMNQHHLNALGVGH 312
Mvk_rat                  SLECERVLG--EMAAAP-------VPEQYLVLEELMDMNQHHLNALGVGH 312
Mvk_H_sapiens            SLECERVLG--EMGEAP-------APEQYLVLEELIDMNQHHLNALGVGH 312
Mvk_P_rhodozyma          ADEAIRCLKDSEMERAV-------MIDR---LQNLVSENHAHLAALGVSH 323
Mvk_S_pombe              SKSAVLALTSES----------DKNSSAKKLGEFIVLNQKLLECLGVSH 307
Mvk_A_pernix             AREALHAIE---------------KGDAERLGLIMNAAQGLLSSLGASS 257
Mvk_P_abyssi             VDKAKEVIISKLDEEEK-----------FLKLGELMNINHGLLDALGVST 267
Mvk_P_horikoshii         VDKAKEIILSKLDEEEK-----------LTKLGELMNINHGLLDALGVST 267
Mvk_P_furiosus           VEKAKDVILSNVDKEEK-----------FERLGVLMNINHGLLDALGVST 266
Mvk_M_thermoautotrophicum TNTAYRELLRNNTEP---------------LGELMNLNQGLLDSMGVST 242
Mvk_A_fulgidus           SLEASDVGSAER------------------LEELIAINQSLLRAIGVSN 230
Mvk_M_jannaschii         IDEALKIKNKED-------------------FGKLMTKNHELLKKLNIST 254
Mvk_P_zeaxanthinifaciens LWDAFAVCTRALEAALLS----------GGSPDAAITENQRLLERIGVVP 298
Mvk_yeast                ALQGLEIMTKLSKCKGTDDEAVETNNELYEQLLELIRINHGLLVSIGVSH 329

Mvk_mouse                NSLDQLCQVTAAH--GLHSKLTGAG-----GGGCGITLLKPGLEQATVEA 355
Mvk_rat                  ASLDQLCQVTAAH--GLHSKLTGAG-----GGGCGITLLKPGLERAKVEA 355
Mvk_H_sapiens            ASLDQLCQVTRAR--GLHSKLTGAG-----GGGCGITLLKPGLEQPEVEA 355
Mvk_P_rhodozyma          PSLEEIIRIGADKPFELRTKLTGAG-----GGGCAVTLVPDDFSTETLQA 368
Mvk_S_pombe              YSIDRVLQATK---SIGWTKLTGAG-----GGGCTITLLTPECKEEEFKL 349
Mvk_A_pernix             LEIETLVYRMRSAG-ALGAKLTGAG-----WGGCVIGLFKEGEVERGLES 301
Mvk_P_abyssi             KKLSELVYAAR-TAGAIGAKLTGAG-----GGGCMYALAP------GKQR 305
Mvk_P_horikoshii         KKLGELVYAAR-TAGAIGAKLTGAG-----GGGCMYALAP------GRQR 305
Mvk_P_furiosus           KKLSELVYAAR-VAGALGAKITGAG-----GGGCMYALAP------NKQR 304
Mvk_M_thermoautotrophicum RELSMMVYEAR-NAGAAGSKITGAG-----GGGSIIAHCP------GCVD 280
Mvk_A_fulgidus           PEIDRTIAELE-RMG-LNAKITGAG-----GGGCIFGLFK------GEKP 267
Mvk_M_jannaschii         PKLDRIVDIGN--RFGFGAKLTGAG-----GGGCVIILVN---------- 287
Mvk_P_zeaxanthinifaciens AATQALVAQIEEAG--GAAKICGAGSVRGDHGGAVLVRIDDAQAMASVMA 346
Mvk_yeast                PGLELIKNLSDDL-RIGSTKLTGAG-----GGGCSLTLLRRDISQEQIDS 373

Mvk_mouse                AKQALT-SCGFDCWETSIGAPGVSTHSAAAVGDP--------------- 388
Mvk_rat                  AKQALT-GCGFDCWETSIGAPGVSMHSATSIEDP--------------- 388
Mvk_H_sapiens            TKQALT-SCGFDCLETSIGAPGVSIHSATSLDSR--------------- 388
Mvk_P_rhodozyma          LMETLV-QSSFAPYIARVGGSGVGFLSSTKADPEDGENRL------KDGL 411
Mvk_S_pombe              CKESLLAHKN-SIYDVQLGGPGVSVVTDSDS-------------FFPQYE 385
Mvk_A_pernix             VVESSS-----QAFTASIAEEGARLEEF--------------------- 324
Mvk_P_abyssi             EVATAIKIAGGTPMITRISKEGLRIEEVRE------------------- 335
Mvk_P_horikoshii         EVATAIKIAGGIPMITRVSREGLRIEEVSR------------------- 335
```

Figure 1 (continued)

```
Mvk_P_furiosus                EVATAIRIAGGTPMITEISREGLKIEEVIK--------------------- 334
Mvk_M_thermoautotrophicum     DVVTALNRN-WKAMRAEFSVKGLI--------------------------- 303
Mvk_A_fulgidus                ----------KGSFIVEPEKEGVRIEE------------------------ 284
Mvk_M_jannaschii              --------EEKEKELLKELNKEDVRIFNCRMMN------------------ 312
Mvk_P_zeaxanthinifaciens      RHPDLDWAPLRMSRTGAAPGPAPRAQPLPGQG------------------- 378
Mvk_yeast                     FXKKLQDDFSYETFETDLGGTGCCLLSAKNLNKDLKIKSLVFQLFENKTT  423

Mvk_mouse                     VRQALG-L------------ 395
Mvk_rat                       VRQALG-L------------ 395
Mvk_H_sapiens                 VQQALDGL------------ 396
Mvk_P_rhodozyma               VGTEIDELDRWALKTGRWS- 430
Mvk_S_pombe                   SDFDFKKLNLLSKFNKYYI- 404
Mvk_A_pernix                  --------------------
Mvk_P_abyssi                  --------------------
Mvk_P_horikoshii              --------------------
Mvk_P_furiosus                --------------------
Mvk_M_thermoautotrophicum     --------------------
Mvk_A_fulgidus                --------------------
Mvk_M_jannaschii              --------------------
Mvk_P_zeaxanthinifaciens      --------------------
Mvk_yeast                     TKQQIDDLLLPGNTNLPWTS 443
```

MODIFIED MEVALONATE KINASE WITH REDUCED FEEDBACK INHIBITION

This application is the US national phase of Int'l Application PCT/EP2005/013282 filed 12 Dec. 2005 which designated the U.S. and claims benefit of EP 04 029 529.7, filed 14 Dec. 2004; the entire contents of which are hereby incorporated by reference.

The present invention provides modified mevalonate kinases that are less sensitive to feedback inhibition. The modified enzymes and polynucleotides encoding the same can be used for the production of isoprenoid compounds, for the treatment of disorders that are characterized by decreased mevalonate kinase activity, and for diagnostic purposes.

Mevalonate kinase (Mvk) is an essential enzyme in the mevalonate pathway which leads to the production of numerous cellular isoprenoids. Isopentenyl diphosphate (IPP), the product of the mevalonate pathway, and the isomeric compound, dimethylallyl diphosphate (DMAPP), are the fundamental building blocks of isoprenoids in all organisms. The isoprenoids include more than 23,000 naturally occurring molecules of both primary and secondary metabolism. The chemical diversity of this natural product class reflects their wide-ranging physiological roles in all living systems. Isoprenoids include, e.g., hopane triterpenes, ubiquinones and menaquinones in bacteria, carotenoids, plastoquinones, mono-, sesqui-, di-, and tri-terpenes, and the prenyl side chains of chlorophylls in plants, and heme A, quinones, dolichols, sterols/steroids and retinoids in mammals. In addition, isoprenoids are involved in isopentenyl tRNAs, in protein prenylation and in cholesterol modification of, e.g., the hedgehog class of cell signaling proteins.

In terms of regulation, HMG-CoA reductase is considered broadly to be the rate-determining enzyme in the mevalonate pathway (e.g., Goldstein and Brown, Nature 343, 425-430, 1990; Weinberger, Trends Endocrinol. Metab. 7, 1-6, 1996; Hampton et al., Trends Biochem. Sci. 21, 140-145, 1996; Houten et al., J. Biol. Chem. 278, 5736-5743, 2003). In line with this view, supplementation of the culture medium with mevalonate has been shown to stimulate carotenoid production in both *Phaffia rhodozyma* (Calo et al., Biotechnol. Lett. 17, 575-578, 1995) and *Haematococcus pluvialis* (Kobayashi et al., J. Ferment. Bioeng. 71, 335-339, 1991). Increasing evidence in recent years, however, indicates that mevalonate kinase is subject to feedback inhibition by, e.g., the downstream products geranyldiphosphate, farnesyldiphosphate and geranylgeranyldiphosphate. This feedback inhibition may also contribute to regulation and rate limitation of the mevalonate pathway and, thus, of isoprenoid biosynthesis in general.

In humans, the importance of mevalonate kinase was demonstrated by the identification of its deficiency as the biochemical and molecular cause of the inherited human disorders mevalonic aciduria and hyperimmunoglobulinemia D and periodic fever syndrome (Houten et al., 2000; Nwokoro et al., Mol. Genet. Metab. 74, 105-119, 2001). The pathophysiology of these disorders is not yet understood, but eventually will give insight into the in vivo role of mevalonate kinase and isoprenoid biosynthesis with respect to the acute phase response and fever. Mevalonate kinase deficiency also seems to be involved, e.g., in Zellweger syndrome and in rhizomelic chondrodysplasia punctata, a disorder of peroxisomal biogenesis wherein a subset of peroxisomal enzymes, including mevalonate kinase, is not transported into peroxisomes (Kelley and Herman, Annu. Rev. Genomics Hum. Genet. 2, 299-341, 2001). Finally, mevalonate kinase was proposed to play a role in cellular proliferation, cell cycle regulation and/or cellular transformation (see Graef et al., Virology 208, 696-703, 1995; Hinson et al., J. Biol. Chem. 272, 26756-26760, 1997).

All mevalonate kinases investigated so far are feedback-inhibited by downstream products of the pathway, e.g. farnesyl pyrophosphate or geranylgeranyl pyrophosphate.

Thus, it is an object of the present invention to provide a modified mevalonate kinase which is less sensitive or resistant to feedback inhibition or with sensitivity to feedback inhibition which is reduced relative to that of the non-modified mevalonate kinase, i.e. having improved catalytical properties. Feedback-resistant mevalonate kinase enzymes may have industrial potential, e.g., (1) in the biotechnological production of all kinds of isoprenoid compounds (e.g., carotenoids, coenzyme Q10, vitamin D, sterols, etc.), (2) as diagnostic enzymes for, e.g., enzymatic measurement of mevalonate concentrations in biological fluids, or (3) as therapeutic enzymes for lowering mevalonate concentrations in patients with mevalonic aciduria. Feedback-resistant mevalonate kinases are particularly suited for biotechnological production of isoprenoids, since they may allow a larger flux through the mevalonate pathway and, thus, higher isoprenoid productivity.

In particular, the present invention relates to a modified mevalonate kinase which exhibits a sensitivity to feedback inhibition which is reduced in comparison to the corresponding non-modified mevalonate kinase wherein
(i) the amino acid sequence of the modified mevalonate kinase contains at least one mutation when compared with the amino acid sequence of the corresponding non-modified mevalonate kinase and
(ii) the at least one mutation is at one or more amino acid position(s) selected from the group consisting of amino acid positions corresponding to positions 55, 59, 66, 83, 106, 111, 117, 142, 152, 158, 218, 231, 249, 367 and 375 of the amino acid sequence of *Saccharomyces cerevisiae* mevalonate kinase as shown in SEQ ID NO:1.

Any enzyme capable of catalyzing the phosphorylation of mevalonate (mevalonic acid) to 5-phosphomevalonate (5-phosphomevalonic acid), or of mevalonate analogues (as, e.g., described by Wilde and Eggerer, Eur. J. Biochem. 221, 463-473, 1994) to the corresponding phosphorylated compounds and which exhibits sensitivity to feedback inhibition may be used as mevalonate kinase for the purpose of the present invention.

The term "wild-type enzyme" or "wild-type mevalonate kinase" thus means any mevalonate kinase which exhibits sensitivity to feedback inhibition which may serve as starting point for designing (more) feedback resistant mutants according to the present invention. Such wild-type enzymes may be for instance mevalonate kinases/mevalonate kinase sequences derivable from nature or variants of synthetic mevalonate kinases, which can be made (more) feedback resistant by any of the teachings of the present invention. Examples of amino acid sequences of such mevalonate kinases include those which can be found in publicly available databases, such as for instance Swiss-Prot. Preferred are such wild-type enzymes which are homologous or identical to any one of the amino acid sequences shown in FIG. 1 or Table 3, including e.g. SEQ ID NOs:1 and 6, or SEQ ID NO:8. Homologous refers to a mevalonate kinase that is at least about 60% identical, preferably at least about 70% identical, more preferably at least about 80% identical, even more preferably at least about 90% identical, most preferably at least about 95% identical to one or more of the amino acid sequences as shown in FIG. 1, including e.g. SEQ ID NOs:1 and 6, or SEQ ID NO:8. The terms "wild-type mevalonate kinase" and "non-modified mevalonate kinase" are used interchangeably herein.

If required, a suitable phosphate donor may be added to afford phosphorylation of mevalonate (or mevalonate analogues). As phosphate donors for mevalonate kinase, different compounds may be conceivable, as for instance ATP, TTP, ITP, GTP, UTP, or CTP (see Gibson et al., Enzyme 41, 47-55, 1989). The most preferred phosphate donor is ATP (adenosine 5'-triphosphate).

The term "% identity", as known in the art, means the degree of relatedness between polypeptide or polynucleotide sequences, as the case may be, as determined by the match between strings of such sequences. "Identity" may be readily determined by known methods of sequence alignments, such as e.g., with the program GAP (GCG Wisconsin Package, version 10.2, Accelrys Inc., 9685 Scranton Road, San Diego, Calif. 92121-3752, USA) using for instance the following parameters: gap creation penalty 8, gap extension penalty 2 (default parameters); with the program "PILEUP" (GCG Wisconsin Package, version 10.2, Accelrys Inc., 9685 Scranton Road, San Diego, Calif. 92121-3752, USA) using for instance the following parameters: gap creation penalty 12, gap extension penalty 4, and blosum62.cmp matrix (default parameters); or with the program ClustalW (Version 1.7, EMBL, Heidelberg, Germany) using BLOSUM exchange matrix. Such sequence alignments are routinely performed by the man skilled in the art (e.g., Cho et al., J. Biol. Chem. 276, 12573-12578, 2001).

With "at least one mutation" it is meant that the modified mevalonate kinase of the present invention may contain one or more mutations, i.e., one, two, three, four, five, six, seven, eight, nine, ten, eleven, twelve, thirteen, fourteen, fifteen, etc. (i.e. and more) mutations, including at least one at a position mentioned above.

For the purpose of the present invention a "mutant", "mutant enzyme", or "mutant mevalonate kinase" may be any variant derivable from a given wild-type enzyme/mevalonate kinase that is (more) feedback resistant or having a reduced sensitivity to feedback inhibition than the respective wild-type enzyme. The mutant(s) may be obtained by any method known in the art, such as for instance site-directed mutagenesis, saturation mutagenesis, random mutagenesis/directed evolution, chemical or UV mutagenesis of entire cells/organisms, designing synthetic genes, and/or by in vitro (cell-free) translation (see, e.g., Jermutus et al., Curr. Opin. Biotechnol. 9, 534-548, 1998; Betton, Curr. Prot. Pept. Sci. 4, 73-80, 2003; Martin et al., Biotechniques 31, 948-953, 2001). It is not relevant how the mutant(s) is/are obtained.

As used herein, the term "feedback inhibition" includes any inhibition of enzymatic activity of mevalonate kinase by a metabolite downstream of mevalonate in isoprenoid biosynthesis. Metabolites downstream of mevalonate in isoprenoid biosynthesis include but are not limited to 5-phosphomevalonate, isopentenyl diphosphate (IPP), 3,3-dimethylallyl diphosphate (DMAPP), geranyl diphosphate (GPP), farnesyl diphosphate (FPP), geranylgeranyl diphosphate (GGPP), farnesol, dolichol phosphate, and phytyl-pyrophosphate (Dorsey and Porter, J. Biol. Chem. 243, 4667-4670, 1968; Flint, Biochem. J. 120, 145-150, 1970; Gray and Kekwick, Biochim. Biophys. Acta 279, 290-296, 1972; Hinson et al., J. Lipid Res. 38, 2216-2223, 1997). Feedback inhibition of mevalonate kinase may be based on allosteric regulation of mevalonate kinase by binding to the enzyme of the metabolite downstream of mevalonate in isoprenoid biosynthesis.

Preferably, the feedback inhibition is feedback inhibition by farnesyl diphosphate (FPP) or geranylgeranyl diphosphate (GGPP). Sensitivity to feedback inhibition means for instance sensitivity to inhibition to physiologically or industrially relevant concentrations of a downstream product of the mevalonate pathway, e.g., FPP or GGPP.

According to the present invention the modified mevalonate kinase exhibits sensitivity to feedback inhibition which is reduced in comparison to the corresponding non-modified mevalonate kinase. Preferably, the sensitivity to feedback inhibition of the modified mevalonate kinase of the invention is reduced by at least about 5%, more preferably at least about 10%, 20%, 25%, 30%, 40%, 50%, 60%, 70%, 80%, 90% or 100% in comparison to the corresponding non-modified mevalonate kinase (for measurement and quantification of feedback resistance, see below). Thus, in other words, the modified mevalonate kinase of the invention may exhibit a feedback resistance of at least about 5%, preferably at least about 10%, 20%, 25%, 30%, 40%, 50%, 60%, 70%, 80%, 90% or 100% when compared with the corresponding non-modified mevalonate kinase.

"Feedback resistance" as used herein may be any increase in resistance to "feedback inhibition" (as defined above). Feedback resistance can be analyzed in different ways known to those skilled in the art. An appropriate example of such an analysis is shortly described herein: mevalonate kinase activity is measured in an activity assay at non-saturating concentrations of for instance ATP (or of another phosphate donor) and mevalonate (or mevalonate analogue), i.e., at for instance ATP (or phosphate donor) and mevalonate (or mevalonate analogue) concentrations around which the reaction rate is sensitive to changes of these substrate concentrations, e.g., at concentrations around the respective $K_m$ values of the enzyme under investigation for these substrates. The activities of both wild-type mevalonate kinase and of a variant/mutant of this enzyme are measured under otherwise identical conditions both in the absence and presence of a relevant concentration of a feedback inhibitor, i.e., at a concentration of feedback inhibitor affording significant inhibition of the wild-type mevalonate kinase. If the extent of inhibition (e.g., % inhibition) by the feedback inhibitor is lower for the mutant than for the wild-type enzyme, then the mutant is feedback resistant in the context of the present patent application. Once a feedback resistant variant/mutant has been identified, the same procedure as described above may be applied to identify further improved mutants, i.e., mutants that are even more feedback resistant. Feedback resistance (%) is calculated as follows: if (a) and (b) are the measured mevalonate kinase activities of the wild-type enzyme in the absence and presence, respectively, of the feedback inhibitor (e.g., FPP), and if (c) and (d) are the measured mevalonate kinase activities of the mutant enzyme in the absence and presence, respectively, of the same feedback inhibitor, then % feedback resistance is:

$$\% \text{ resistance} = 100 \cdot ((d/c) - (b/a))/(1 - (b/a))$$

Preferably, the feedback resistance refers to the experimental conditions described in Example 1 of this application. Approximately 3-30 mU/ml (corresponding to ca. 40-400 ng/ml of *Saccharomyces cerevisiae* mevalonate kinase), preferably ca. 10-20 mU/ml of mevalonate kinase activity, and optionally 1 µM FPP may be present in the assay mixture, and the reaction may be carried out at 25° C.

The amino acid sequence of a modified mevalonate kinase of the invention contains at least one mutation when compared with the amino acid sequence of the corresponding non-modified mevalonate kinase. The at least one mutation may be for instance an addition, deletion and/or substitution. Preferably, the at least one mutation is an amino acid substitution wherein a given amino acid present in the amino acid sequence of the non-modified mevalonate kinase is replaced with a different amino acid in the amino acid sequence of the modified mevalonate kinase of the invention. The amino acid sequence of a modified mevalonate kinase may contain at least one amino acid substitution when compared with the amino acid sequence of the corresponding non-modified mevalonate kinase. In further embodiments, the modified mevalonate kinase contains at least two, at least three, at least four or at least five substitutions when compared with the amino acid sequence of the corresponding non-modified mevalonate kinase. In other embodiments of the invention, the modified mevalonate kinase contains one to fifteen, one to twelve, one to ten, one to seven, one to five, one to four, two to fifteen, two to twelve, two to ten, two to seven, two to five, two to four, three to fifteen, three to twelve, three to ten, three to seven, three to five or three to four amino acid substitutions when compared with the amino acid sequence of the corresponding non-modified mevalonate kinase.

According to the present invention the at least one mutation is at one or more amino acid position(s) selected from the group consisting of amino acid positions corresponding to positions 55, 59, 66, 83, 106, 111, 117, 142, 152, 158, 218, 231, 249, 367 and 375 of the amino acid sequence of Saccharomyces cerevisiae mevalonate kinase as shown in SEQ ID NO:1. Any combination of mutations at these amino acid positions of SEQ ID NO: 1, i.e. a mutation at positions corresponding to at least two, at least three, at least four, at least five, at least six, at least seven, at least eight, at least nine, at least ten, at least eleven, at least twelve, at least thirteen, at least fourteen or to at least all 15 of the amino acid positions mentioned above may be selected as target for the at least one mutation to generate a modified mevalonate kinase as defined above. Preferably, the present invention provides a modified mevalonate kinase originating from S. cerevisiae, wherein the amino acid sequence of said modified mevalonate kinase comprises at least one mutation, said mutation(s) including one or more mutation(s) at positions 55, 59, 66, 83, 106, 111, 117, 142, 152, 158, 218, 231, 249, 367 and/or 375 as shown in SEQ ID NO:1, wherein SEQ ID NO:1 represents the wild-type amino acid sequence.

Since a modified mevalonate kinase as of the present invention contains at least one mutation at one or more amino acid position(s) as defined above, it may contain further mutation(s) at amino acid position(s) besides the one(s) listed above.

In one aspect, the present invention relates to a modified mevalonate kinase which exhibits a sensitivity to feedback inhibition which is reduced in comparison to the corresponding non-modified mevalonate kinase wherein
(i) the amino acid sequence of the modified mevalonate kinase comprises one or more mutation(s) when compared with the amino acid sequence of the corresponding non-modified mevalonate kinase and
(ii) the one or more mutation(s) is/are at one or more amino acid position(s) selected from the group consisting of amino acid positions corresponding to positions 55, 59, 66, 83, 106, 111, 117, 142, 152, 158, 218, 231, 249, 367 and 375 of the amino acid sequence of Saccharomyces cerevisiae mevalonate kinase as shown in SEQ ID NO:1.

Any combination of these positions shown in SEQ ID NO:1, i.e. two, three, four, five, six, seven, eight, nine, ten, eleven, twelve, thirteen, fourteen or all 15 positions corresponding to the positions mentioned above may be selected as target for mutations to generate said modified mevalonate kinase.

In one embodiment the at least one mutation is at one or more amino acid position(s) selected from the group consisting of amino acid positions corresponding to positions 55, 59, 66, 117, and 152 of the amino acid sequence of Saccharomyces cerevisiae mevalonate kinase as shown in SEQ ID NO:1.

The modified mevalonate kinase may contain only a single mutation, such as for instance a single amino acid substitution, when compared to the corresponding non-modified mevalonate kinase. Preferably, the single mutation is at a position selected from the group consisting of positions corresponding to the amino acid positions 55, 59, 66, 117, and 152 of SEQ ID NO:1. More preferably, the single mutation is an amino acid substitution, such as for instance P55L, F59S, N66K, C117S, or I152M. Most preferably, the substitution is F59S, i.e. a substitution/replacement of phenylalanine with serine on a position corresponding to position 59 of SEQ ID NO:1.

The modified mevalonate kinase may contain at least two mutations, such as for instance two amino acid substitutions, when compared to the corresponding non-modified mevalonate kinase. Preferably, one of the at least two mutations, e.g. amino acid substitutions, is at an amino acid position corresponding to a position of SEQ ID NO:1 which is selected from position 55, 66, 83, 106, 111, 117, 152, 218, 249, and/or 375. In case of two mutations, e.g. amino acid substitutions, it is preferred that the two mutations are at positions corresponding to combinations of positions 55/117, 66/152, 83/249, 111/375 or 106/218 of SEQ ID NO:1. More preferably, the two mutations consist of one or two amino acid substitution(s), even more preferably two amino acid substitutions. Most preferred are combinations of two amino acid substitutions/replacements corresponding to combinations of positions of SEQ ID NO:1 which are selected from P55L/C117S, N66K/I152M, K83E/S249P, H111N/K375N or L106P/S218P.

In a particularly preferred embodiment, the modified mevalonate kinase contains two amino acid substitutions corresponding to the combination N66K/I152M of the amino acid sequence shown in SEQ ID NO:1. More preferably, the two amino acid substitutions are N66K and I152M in the non-modified S. cerevisiae mevalonate kinase amino acid sequence as shown in SEQ ID NO:1.

The modified mevalonate kinase may contain at least four mutations, such as for instance four amino acid substitutions, when compared to the corresponding non-modified mevalonate kinase. Preferably, one of the at least four mutations, e.g. amino acid substitutions, is at an amino acid position corresponding to a position of SEQ ID NO:1 which is selected from position 142, 158, 231, and 367. In case of four mutations, e.g. amino acid substitutions, it is preferred that the four mutations are at positions corresponding to a combination of positions 142/158/231/367 of SEQ ID NO:1. More preferably, the four mutations consist of one, two, three or four amino acid substitutions, even more preferably four amino acid substitutions. Most preferred is a combination of four amino acid substitutions corresponding to positions 142/158/231/367 of SEQ ID NO:1 which is I142N/L158S/L231I/T367S.

Most preferred are the combinations of mutations disclosed in Table 1 (see infra). The amino acid positions identified in the examples may be transferred to mevalonate kinases of different origin.

A modified mevalonate kinase of the invention may be obtained by introducing a mutation to the corresponding non-modified mevalonate kinase.

The non-modified mevalonate kinase may be of eukaryotic or prokaryotic origin, such as for instance animals including humans, plants, algae, fungi including yeast, and bacteria. Preferably, the non-modified mevalonate kinase is selected from fungi including yeast or from bacteria, more preferably selected from the group consisting of *Aspergillus, Saccharomyces, Paracoccus, Rhodobacter* and *Phaffia*. Even more preferred are *Aspergillus niger, Saccharomyces cerevisiae, Paracoccus zeaxanthinifaciens, Rhodobacter sphaeroides*, such as *R. sphaeroides* ATCC 35053, or *Phaffia rhodozyma*, with *Saccharomyces cerevisiae* being most preferred.

In one aspect of the present invention, the non-modified mevalonate kinase is feedback inhibited by FPP. Feedback inhibition of the non-modified mevalonate kinase by FPP may be for instance at least about 10%, 20%, 30%, 40%, 50%, 60%, 70%, 80%, or 90%, as determined by a method known to the skilled person, such as for instance as described by Popják (Meth. Enzymol. 15, 393-, 1969), Gibson et al. (Enzyme 41, 47-55, 1989), Hinson et al. (J. Lipid Res. 38, 2216-2223, 1997), Schulte et al. (Anal. Biochem. 269, 245-254, 1999), or Cho et al. (J. Biol. Chem. 276, 12573-12578, 2001). A particular assay is described in Example 1 using different FPP concentrations.

The modified mevalonate kinase of the invention may comprise foreign amino acids, preferably at its N- or C-terminus. "Foreign amino acids" mean amino acids which are not present in a native (occurring in nature) mevalonate kinase, such as for instance a stretch of at least about 3, preferably at least about 5 and more preferably at least about 7 contiguous amino acids which are not present in a native mevalonate kinase. Suitable stretches of foreign amino acids include but are not limited to "tags" that facilitate purification of the recombinantly produced modified mevalonate kinase. Examples of such tags include but are not limited to a $His_6$ tag, a FLAG tag, a myc tag, and the like.

In another embodiment the modified mevalonate kinase may contain one or more deletion(s), e.g. two deletions, when compared with the amino acid sequence of the corresponding non-modified mevalonate kinase. Preferably, the deletions affect N- or C-terminal amino acids of the corresponding non-modified mevalonate kinase and do not significantly reduce the functional properties, e.g., the specific activity, of the enzyme.

The modified mevalonate kinase of the invention usually is a non-naturally occurring mevalonate kinase. The specific activity of the modified mevalonate kinase may be for instance at least about 10%, preferably at least 20%, 30%, 35%, 40%, 50%, 60%, 70%, 80%, 90%, 100% and even more, such as for instance about 150%, 200% and more of the specific activity of the corresponding non-modified mevalonate kinase.

Methods for measuring specific activity are known to the man skilled in the art. The specific activity may for instance be determined via measuring the consumption of NADH. Suitable conditions for such measurement may be those as e.g. outlined in Example 1 except that, typically, saturating substrate concentrations are used or, in the case of enzyme inhibition at high substrate concentrations, at substrate concentrations that provide maximal activity under the particular experimental conditions.

The invention further relates to a polynucleotide comprising a nucleotide sequence which codes for a modified mevalonate kinase according to the invention. Any polyribonucleotide or polydeoxyribonucleotide such as for instance unmodified RNA or DNA or modified RNA or DNA may be used as polynucleotide. Polynucleotides include but are not limited to single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. As used herein, a polynucleotide may further include DNA or RNA that comprises one or more unusual base(s), e.g., inosine, or one or more modified base(s), e.g., tritylated bases.

A polynucleotide of the invention may easily be obtained by modifying a polynucleotide sequence which codes for a non-modified mevalonate kinase, e.g. constructed by starting from genomic or cDNA sequences coding for mevalonate kinases known in the state of the art [for sequence information see, e.g., the relevant sequence databases, for example Genbank (Intelligenetics, California, USA), European Bioinformatics Institute (Hinston Hall, Cambridge, GB), NBRF (Georgetown University, Medical Centre, Washington D.C., USA) and Vecbase (University of Wisconsin, Biotechnology Centre, Madison, Wis., USA)] by mutagenesis methods known in the art, such as for instance introducing mutations such as, e.g., additions, deletions and/or substitutions into the nucleotide sequences coding for non-modified mevalonate kinases by for instance site-directed mutagenesis and PCR-based methods (see e.g. Sambrook et al., Molecular Cloning, Cold Spring Harbor Laboratory Press, New York).

The principles of the polymerase chain reaction (PCR) method are outlined, e.g., by White et al., Trends Genet. 5, 185-189, 1989, whereas improved methods are described, e.g., in Innis et al. [PCR Protocols: A guide to Methods and Applications, Academic Press, Inc. (1990)].

The generation of modified mevalonate kinases may be performed by site-directed mutagenesis, a method which is originally outlined by Hutchison and Edgell (J. Virol. 8, 181-189, 1971), involving the annealing of a synthetic oligonucleotide carrying the desired nucleotide substitution, deletion or addition to a target region of a single-stranded DNA sequence wherein the mutation should be introduced (for review see Smith, Annu. Rev. Genet. 19, 423-462, 1985; and for improved methods see references 2-6 in Stanssen et al., Nucl. Acids Res. 17, 4441-4454, 1989). DNA as starting material can be isolated by methods known in the art and described, e.g., in Sambrook et al. (Molecular Cloning) from the respective strains/organisms. It is, however, understood that DNA encoding a mevalonate kinase to be constructed/mutated in accordance with the present invention may also be prepared on the basis of a known DNA sequence, e.g. by construction of a synthetic gene by methods known in the art (as described, e.g., in EP 747 483 and by Lehmann et al., Prot. Eng. 13, 49-57, 2000). A non-limiting example of a polynucleotide encoding a modified mevalonate kinase according to the invention is shown in SEQ ID NO:5.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a nucleic acid includes some or all of the 5'-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state. Conventional nucleic acid purification methods known to skilled artisans may be used to obtain isolated polynucleotides.

An isolated polypeptide may be a polypeptide which is substantially free of other polypeptides. An isolated polypeptide may be for instance greater than 80% pure, preferably greater than 90% pure, more preferably greater than 95% pure, and most preferably greater than 99% pure. Purity may be determined according to methods known in the art, e.g., by SDS-PAGE and subsequent protein staining. Protein bands may be quantified by for instance densitometry. Further methods for determining the purity are within the level of ordinary skill.

In yet another embodiment the invention pertains to a vector or plasmid comprising a polynucleotide according to the invention. The vector or plasmid preferably comprises at least one marker gene. The vector or plasmid may further comprise regulatory elements operably linked to the polynucleotide of the invention. The term "operably linked" as used herein refers for instance to the association of nucleic acid sequences on a single nucleic acid fragment so that the function of one is affected by the other. For example, a promoter is operably linked with a coding sequence when it is capable of affecting the expression of that coding sequence, i.e., the coding sequence is under the transcriptional control of the promoter. Coding sequences may be operably linked to regulatory sequences in sense or antisense orientation. The term "expression" denotes the transcription of a DNA sequence into mRNA and/or the translation of mRNA into an amino acid sequence. The term "overexpression" means for instance the production of a gene product in a modified organism (e.g., modified by transformation or transfection) that exceeds levels of production in the corresponding non-modified organism.

Integration of DNA sequences encoding modified mevalonate kinases as of the present invention into vectors for overexpressing the encoded polypeptides in an appropriate host system may be performed by methods known in the art and described in, e.g., Sambrook et al. (s.a.). Either the DNA sequences themselves or a vector/plasmid comprising a DNA sequence as of the present invention may be used to transform the suitable host systems of the invention to get (over-) expression of the encoded polypeptide. Suitable host systems useful for the present invention may be selected from eukaryotic or prokaryotic cells, for instance cells of animals including humans, plants, bacteria, or fungi including yeast. Examples of such host cells include but are not limited to cells selected from streptococci, staphylococci, enterococci, cyanobacteria, yeast (e.g. *Saccharomyces*), basidiomycetes, gymnosperms, angiosperms, or cell-lines such as for instance *Drosophila* S2, *Spodoptera* Sf9, CHO, COS, HeLa, 3T3, BHK, HK293 [human kidney 293 cell line???], and CV-1.

Suitable methods for the expression in plants are described, e.g., by Pen et al. in Bio/Technology 11, 811-814, 1994 or in EP 449 375, preferably in seeds as described, e.g., in EP 449 376. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences of the present invention should be capable of promoting expression of the present gene product. High level plant promoters that may be used in this invention include for instance the promoter of the small subunit (ss) of the ribulose-1,5-bisphosphate carboxylase, for example from soybean (Berry-Lowe et al., J. Mol. Appl. Genet. 1, 483-498, 1982), and the promoter of the chlorophyll a/b binding protein.

A fungal host cell within the scope of the present invention may be for instance selected from Aspergilli, such as *Aspergillus niger* or *Aspergillus oryzae*, *Trichoderma*, such as *Trichoderma reesei*, *Saccharomyces*, such as *Saccharomyces cerevisiae*, *Pichia*, such as *Pichia pastoris*, or *Hansenula*, such as *Hansenula polymorpha*, preferably *H. polymorpha* DSM 5215. A bacterial host cell within the scope of the present invention may be for instance selected from *Paracoccus*, such as *Paracoccus zeaxanthinifaciens*, *Rhodobacter*, such as *R. sphaeroides*, *Escherichia*, such as *E. coli*, *Bacillus*, such as *Bacillus subtilis*, *Streptomyces*, such as *Streptomyces lividans* (see e.g. Anne and van Mellaert in FEMS Microbiol. Lett. 114, 121-128, 1993). Preferred strains of *E. coli* which may be used are selected from e.g., *E. coli* K12 strains, such as for instance M15 (described as DZ 291 by Villarejo et al. in J. Bacteriol. 120, 466-474, 1974), HB 101 (ATCC No. 33694) or *E. coli* SG13009 (Gottesman et al., J. Bacteriol. 148, 265-273, 1981). The man skilled in the art knows that such suitable hosts may be available from any known depository authority, as listed for instance in the Journal "Industrial Property" (vol. 1, pages 29-40, 1991) or in the Official Journal of the European Patent Office (vol. 4, pages 155/156, 2003).

Depending on the host system, different vectors may be used, said vectors comprising a polynucleotide according to the invention. Non-limiting examples of vectors which may be used for expression in fungi are known in the art and described e.g. in EP 420 358, or by Cullen et al. (Bio/Technology 5, 369-376, 1987), Ward (in Molecular Industrial Mycology, Systems and Applications for Filamentous Fungi, Marcel Dekker, New York, 1991), Upshall et al. (Bio/Technology 5, 1301-1304, 1987), Gwynne et al. (Bio/Technology 5, 71-79, 1987), or Punt et al. (J. Biotechnol. 17, 19-34, 1991), and for yeast by Sreekrishna et al. (J. Basic Microbiol. 28, 265-278, 1988; Biochemistry 28, 4117-4125, 1989), Hitzemann et al. (Nature 293, 717-722, 1981) or in EP 183 070, EP 183 071, EP 248 227, EP 263 311. Non-limiting examples of vectors which may be used for expression in *E. coli* are mentioned, e.g., by Sambrook et al. [s.a.] or by Fiers et al. in Proc. 8th Int. Biotechnol. Symp. [Soc. Franc. de Microbiol., Paris (Durand et al., eds.), pp. 680-697, 1988], Bujard et al. (in Meth. Enzymol., eds. Wu and Grossmann, Academic Press, Inc., Vol. 155, 416-433, 1987), or Stüber et al. (in Immunological Methods, eds. Lefkovits and Pernis, Academic Press, Inc., Vol. IV, 121-152, 1990). Non-limiting examples of vectors which may be used for expression in Bacilli are known in the art and described, e.g. in EP 207 459 or EP 405 370, by Yansura and Henner in Proc. Natl. Acad. Sci. USA 81, 439-443 (1984), or by Henner, Le Grice and Nagarajan in Meth. Enzymol. 185, 199-228, 1990. Non-limiting examples of vectors which may be used for expression in *H. polymorpha* are known in the art and described, e.g., in Gellissen et al., Biotechnology 9, 291-295, 1991.

Either such vectors already carry regulatory elements, e.g. promoters, or the DNA sequences of the present invention can be engineered to contain such elements. Suitable promoter elements which may be used are known in the art and are, e.g., for *Trichodemia reesei* the cbh1- (Haarki et al., Biotechnology 7, 596-600, 1989) or the pki1-promoter (Schindler et al., Gene 130, 271-275, 1993), for *Aspergillus oryzae* the amy-promoter [Christensen et al., Abstr. 19th Lunteren Lectures on Molecular Genetics F23 (1987); Christensen et al., Biotechnology 6, 1419-1422, 1988; Tada et al., Mol. Gen. Genet. 229, 301-306, 1991], for *Aspergillus niger* the glaA- (Cullen et al., Bio/Technology 5, 369-376, 1987; Gwynne et al., Bio/Technology 5, 713-719, 1987; Ward in Molecular Industrial Mycology, Systems and Applications for Filamentous Fungi, Marcel Dekker, New York, 83-106, 1991), alcA- (Gwynne et al., Bio/Technology 5, 718-719, 1987), suc1- (Boddy et al., Curr. Genet. 24, 60-66, 1993), aphA- (MacRae et al., Gene 71, 339-348, 1988; MacRae et al., Gene 132, 193-198, 1993), tpiA- (McKnight et al., Cell 46, 143-147, 1986; Upshall et al., Bio/Technology 5, 1301-1304, 1987), gpdA- (Punt et al., Gene 69, 49-57, 1988; Punt et al., J. Biotechnol. 17, 19-37, 1991) and the pkiA-promoter (de Graaff et al., Curr. Genet. 22, 21-27, 1992). Suitable promoter elements which may be used for expression in yeast are known in the art and are, e.g., the phoS-promoter (Vogel et al., Mol. Cell. Biol. 9, 2050-2057, 1989; Rudolf and Hinnen, Proc. Natl. Acad. Sci. USA 84, 1340-1344, 1987) or the gap-promoter for expression in *Saccharomyces cerevisiae*, and e.g. the aox1-promoter for *Pichia pastoris* (Koutz et al., Yeast 5, 167-177, 1989; Sreekrishna et al., J. Basic Microbiol. 28, 265-278, 1988), or the FMD promoter (Hollenberg et al., EPA No. 0299108) or MOX promoter (Ledeboer et al., Nucleic Acids Res. 13, 3063-3082, 1985) for *H. polymorpha*.

Suitable promoters include natural and synthetic promoters as for instance described in Giacomini et al. (Gene 144, 17-24, 1994). Appropriate teachings for expression of a claimed (mutant) mevalonate kinase in bacteria, either by appropriate plasmids or through integration of mevalonate kinase-encoding DNA sequences into the chromosomal DNA, can be found in many places, e.g., U.S. Pat. No. 6,322,995.

The invention further relates to a method/process for producing a modified mevalonate kinase of the invention comprising:
(a) culturing a host cell of the invention under conditions that allow expression of the modified mevalonate kinase of the invention; and
(b) recovering the modified mevalonate kinase from the cells or from the medium.

The modified mevalonate kinase of the invention may be prepared from genetically engineered host cells.

For recombinant production of the polypeptides of the invention, host cells may be genetically engineered to incorporate polynucleotides or vectors or plasmids of the invention. Introduction of a polynucleotide or vector into the host cell may be effected by methods described in many standard laboratory manuals such as for instance calcium phosphate transfection, DEAE-dextran mediated transfection, microinjection, cationic lipid-mediated transfection, electroporation, transduction, ballistic introduction and infection [for reference, see, e.g., Davis et al., Basic Methods in Molecular Biology (1986), and Sambrook et al., Molecular Cloning: A Laboratory Manual, 2nd Ed., Cold Spring Harbor Laboratory Press, Cold Spring Harbor, N.Y. (1989)].

Any system or vector suitable to maintain, propagate or express polynucleotides and/or to express a polypeptide in a host may be used for expression/production of the mevalonate kinases of the invention, including, among others, those described supra.

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention may be recovered and purified from recombinant cell cultures by well-known methods including for instance ammonium sulfate or ethanol precipitation, acid extraction, anion or cation exchange chromatography, phosphocellulose chromatography, hydrophobic interaction chromatography, affinity chromatography, and hydroxyapatite chromatography. In one embodiment, high performance liquid chromatography is employed for purification. Well-known techniques for protein refolding may be employed to regenerate active conformation when the polypeptide is denatured during isolation and/or purification. Methods of protein purification are described in, e.g., Deutscher, Protein Purification, Academic Press, New York, 1990; and Scopes, Protein Purification, Springer Verlag, Heidelberg, 1994.

A variety of culture methodologies may be applied to produce the proteins of the present invention. For example, large-scale production of a specific gene product, overexpressed from a recombinant microbial host may be produced by for instance batch, fed-batch, continuous or semi-continuous culture methodologies. Details of the various culture methods may be found in, e.g., Thomas D. Brock in Biotechnology: A Textbook of Industrial Microbiology, Second Edition (1989) Sinauer Associates, Inc., Sunderland, Mass., or Deshpande, Appl. Biochem. Biotechnol. 36, 227-234, 1992.

The fermentation media may contain suitable carbon substrates including but not limited to monosaccharides such as glucose and fructose, oligosaccharides such as lactose or sucrose, polysaccharides such as starch or cellulose or mixtures thereof and unpurified mixtures from renewable feedstocks. It is contemplated that the source of carbon utilized in the present invention may encompass a wide variety of carbon containing substrates and is depending on the choice of organism.

The invention further relates to a method/process for the preparation of a modified mevalonate kinase having reduced sensitivity to feedback inhibition, comprising the following steps:
(a) providing a polynucleotide encoding a first mevalonate kinase which exhibits sensitivity to feedback inhibition;
(b) introducing one or more mutation(s) into the polynucleotide sequence such that the mutated polynucleotide sequence encodes a second mevalonate kinase which contains at least one amino acid mutation when compared to the first mevalonate kinase wherein the at least one amino acid mutation is at one or more amino acid position(s) selected from the group consisting of amino acid positions corresponding to positions 55, 59, 66, 83, 106, 111, 117, 142, 152, 158, 218, 231, 249, 367 and 375 of the amino acid sequence of *Saccharomyces cerevisiae* mevalonate kinase as shown in SEQ ID NO:1;
(c) optionally inserting the mutated polynucleotide in a vector or plasmid;
(d) introducing the polynucleotide of step (b) or (c) into a suitable host cell; and (e) culturing the host cell under conditions that allow expression of the modified mevalonate kinase having reduced sensitivity to feedback inhibition.

The preferred embodiments of this method correspond to the preferred embodiments of the modified mevalonate kinase, the polynucleotides encoding them, the vectors and plasmids, the host cells, and the methods described herein. The first and second mevalonate kinase correspond to the non-modified and modified mevalonate kinase, respectively (see supra).

The invention further relates to a method or process for producing an isoprenoid comprising:
(a) culturing the host cell of the invention in a suitable medium under conditions that allow expression of the modified mevalonate kinase in the host cell; and
(b) optionally separating the isoprenoid from the medium.

Preferably, a modified mevalonate kinase of the present invention is used for increasing the production of an isoprenoid.

Such a method/process may be used for the biotechnological production of any type of isoprenoid or isoprenoid compound. Any metabolite(s) and prenylated macromolecule(s) derivable from mevalonate may be used as isoprenoids in the context of this patent application. These isoprenoids may be generated from either natural or non-natural pathways (i.e., pathways not occurring in nature, but engineered biotechnologically), preferably biochemical pathways. Non-limiting examples of such isoprenoids include hopane triterpenes, quinones, carotenoids, mono-, sesqui-, di-, and triterpenes, the prenyl side chains of chlorophylls, heme A, dolichols, sterols/steroids, retinoids, and rubber or rubber derivatives, preferably natural rubber (=cis-1,4-polyisoprene; Mooibroek & Cornish, Appl. Microbiol. Biotechnol. 53, 355-365, 2000).

Quinones within the scope of this invention may be selected from e.g. ubiquinone (=coenzyme Q), menaquinone, plastoquinones and anthraquinones, preferably coenzyme Q6, coenzyme Q7, coenzyme Q8, coenzyme Q9, coenzyme Q10 or coenzyme Q11, and most preferably coenzyme Q10 (Clarke, Protoplasma 213, 134-147, 2000; Han et al., Plant Cell Tissue Organ Culture 67, 201-220, 2001; Kawamukai, J. Biosci. Bioeng. 94, 511-517, 2002). Carotenoids within the scope of this invention may be selected from e.g. phytoene, lycopene, α-, β- and γ-carotene, lutein, zeaxanthin, β-cryptoxanthin, adonixanthin, echinenone, canthaxanthin, astaxanthin and derivatives thereof (Misawa & Shimada, J. Biotechnol. 59, 169-181, 1998; Miura et al., Appl. Environ. Microbiol. 64, 1226-1229, 1998; Hirschberg, Curr. Opin. Biotechnol. 10, 186-191, 1999; Margalith, Appl. Microbiol. Biotechnol. 51, 431-438, 1999; Schmidt-Dannert, Curr. Opin. Biotechnol. 11, 255-261, 2000; Sandmann, Arch. Biochem. Biophys. 385, 4-12, 2001; Lee & Schmidt-Dannert, Appl. Microbiol. Biotechnol. 60, 1-11, 2002). Sterols within the scope of this invention may be selected from e.g. ergosterol, cholesterol, hydrocortisone (Menard Szczebara et al., Nature Biotechnol. 21, 143-149, 2003), vitamin D, 25-hydroxy-vitamin D3, dietary phytosterols (Ling & Jones, Life Sci. 57, 195-206, 1995) and natural surfactants (Holmberg, Curr. Opin. Colloid. Interface Sci. 6, 148-159, 2001) and derivatives thereof.

Suitable host cells for the production of isoprenoids or isoprenoid compounds as defined above may be all types of organisms that are amenable to genetic modification such as, for instance, bacteria, fungi including yeast, algae, plants or animal cells including human cells. These host cells may be the same as defined above for the expression of a modified mevalonate kinase of the present invention. Methods of genetic and metabolic engineering are known to the man skilled in the art (e.g., Verpoorte et al., Biotechnol. Lett. 21, 467-479, 1999; Verpoorte et al., Transgenic Res. 9, 323-343, 2000; Barkovich & Liao, Metab. Eng. 3, 27-39, 2001). Similarly, (potentially) suitable purification methods for isoprenoids and isoprenoid compounds are well known in the art.

The method/process for biotechnological production of an isoprenoid according to the present invention may be performed by for instance whole-cellular fermentation processes as described above, permeabilized host cells, crude cell extracts, cell extracts clarified from cell remnants by any suitable method, e.g., centrifugation or filtration, or even reconstituted reaction pathways with isolated enzymes. Also combinations of such processes are in the scope of the present invention. In the case of cell-free biosynthesis (such as for instance with reconstituted reaction pathways), it is irrelevant how the enzyme has been prepared, such as, for instance, by isolation from a host cell, by in vitro transcription/translation, or by still other means known in the art.

The production of an isoprenoid, such as for instance coenzyme Q10, using a modified Mvk as described above may be increased by for instance at least about 1%, 2%, 5%, 10%, 15%, 20%, 30% or more when compared to the production of the same isoprenoid using a non-modified Mvk. One way of measuring the concentration of isoprenoid compounds in a given sample is described in Example 5.

Another aspect of the invention is the use of a modified mevalonate kinase of the invention or a polynucleotide of the invention for the manufacture of a medicament for the treatment of a disorder associated with decreased activity of mevalonate kinase. Such disorders include but are not limited to mevalonic aciduria, or hyperimmunoglobulinemia D and periodic fever syndrome. It is preferred that a modified mevalonate kinase of the invention is administered as a therapeutic enzyme. Suitable modes of administration may be for instance oral, parenteral, intraperitoneal and/or subcutaneous administration. The modified mevalonate kinases of the invention may be formulated as pharmaceutical compositions (e.g. granules, enzyme crystals, tablets, pills, capsules, injections, solutions, and the like) comprising at least one such enzyme alone or in admixture with for instance pharmaceutically acceptable carriers, excipients and/or diluents. The pharmaceutical compositions may be formulated in accordance with a conventional method. Specific dose levels for any particular patient may be employed depending upon a variety of factors including for instance the activity of specific compounds employed, the age, body weight, general health, sex, diet, time of administration, route of administration, rate of excretion, drug combination, and the severity of the particular disease undergoing therapy.

The polynucleotides of the invention may be used in a gene therapy protocol.

Yet another aspect of the invention is the use of a modified mevalonate kinase of the invention or a polynucleotide of the invention for determining the concentration of mevalonate in biological fluids. Non-limiting examples of biological fluids include blood, serum, plasma, cerebrospinal fluid, urine, tears, sweat, as well as any other intracellular, intercellular and/or extracellular fluids.

It is an object of the present invention to provide a polynucleotide comprising a nucleic acid sequence coding for a modified mevalonate kinase as described above, a vector, preferably an expression vector, comprising such a polynucleotide, a host cell which has been transformed by such a polynucleotide or vector, a process for the preparation of a mevalonate kinase of the present invention wherein the host cell as described above is cultured under suitable culture conditions and the mevalonate kinase is isolated from such host cell or the culture medium by methods known in the art, and a process for the biotechnological production of isoprenoid(s) based on a host cell which has been transformed by such a polynucleotide or vector, and/or which may have stably integrated such a polynucleotide into its chromosome(s).

It is also an object of the present invention to provide (i) a DNA sequence which codes for a mevalonate kinase carrying at least one of the specific mutations of the present invention and which hybridizes under standard conditions with any of the DNA sequences of the specific modified mevalonate kinases of the present invention, or (ii) a DNA sequence which codes for a mevalonate kinase carrying at least one of the specific mutations of the present invention but, because of the degeneracy of the genetic code, does not hybridize but which codes for a polypeptide with exactly the same amino acid sequence as a DNA sequence which hybridizes under standard conditions with any of the DNA sequences of the specific modified mevalonate kinases of the present invention, or (iii) a DNA sequence which is a fragment of such DNA sequences which maintains the activity properties of the polypeptide of which it is a fragment.

"Standard conditions" for hybridization mean in the context the conditions which are generally used by a man skilled in the art to detect specific hybridization signals and which are described, e.g. by Sambrook et al., "Molecular Cloning", second edition, Cold Spring Harbor Laboratory Press 1989, New York, or preferably so-called stringent hybridization and non-stringent washing conditions or more preferably so-called stringent hybridization and stringent washing conditions a man skilled in the art is familiar with and which are described, e.g., in Sambrook et al. (s.a.). A specific example of stringent hybridization conditions is overnight incubation (e.g., 15 hours) at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml of denatured, sheared salmon sperm DNA, followed by washing the hybridization support in 0.1×SSC at about 65° C. for 3×10 min.

It is furthermore an object of the present invention to provide a DNA sequence which can be obtained by the so-called polymerase chain reaction method (PCR) by suitable primers designed on the basis of the specifically described DNA sequences of the present invention. It is understood that a so obtained DNA sequence codes for a mevalonate kinase with at least the same mutation(s) as the ones from which they are designed and show comparable activity properties.

The various embodiments of the invention described herein may be cross-combined.

BRIEF DESCRIPTION OF THE DRAWING

FIG. 1: Multiple sequence alignment calculated with the program ClustalW (version 1.82, EMBL, Heidelberg, Germany) of mevalonate kinase sequences from various sources (accession numbers and sequence ID numbers, respectively, of the corresponding amino acid/nucleotide sequences are indicated): mouse (Swiss-Prot accession no. Q9R008/Genbank accession no. AF137598 (SEQ ID NO:31)), rat (Swiss-Prot accession no. P17256/Genbank accession no. M29472 (SEQ ID NO:32)), human (*H_sapiens*; Swiss-Prot accession no. Q03426/Genbank accession no. M88468 (SEQ ID NO:33)), *Phaffia rhodozyma* (*P_rhodozyma*; SEQ ID NOs: 8/9), *Schizosaccharomyces pombe* (*S_pombe*; Swiss-Prot accession no. Q09780/Genbank accession no. AB000541 (SEQ ID NO:34)), *Saccharomyces cerevisiae* (yeast; Swiss-prot accession P07277/Genbank accession no. NP013935; SEQ ID NOs:1/2), *Aeropyrum pernix* (*A_pernix*; Swiss-Prot accession no. Q9Y946/Genbank accession no. AP000064 (SEQ ID NO:35)), *Pyrococcus abyssi* (*P_abyssi*; Swiss-Prot accession no. Q9V187/Genbank accession no. AJ248284 (SEQ ID NO:36)), *Pyrococcus horikoshii* (*P_horikoshii*; Swiss-Prot accession no. O59291/Genbank accession no. AB009515(SEQ ID NO:37)), *Pyrococcus furiosus* (*P_furiosus*; Swiss-Prot accession no. Q8U0F3/Genbank accession no. AE010263 (SEQ ID NO:38)), *Methanobacterium thermoautotrophicum* (*M_thermoautotrophicum*; Swiss-Prot accession no. Q50559/Genbank accession no. U47134 (SEQ ID NO:39)), *Archaeoglobus fulgidus* (*A_fulgidus*; Swiss-Prot accession no. O27995/Genbank accession no. AE000946 (SEQ ID NO:40)), *Methanococcus jannaschii* (*M_jannaschii*; Swiss-Prot accession no. Q58487/Genbank accession no. U67551 (SEQ ID NO:41)), and *Paracoccus zeaxanthinifaciens* (*P_zeaxanthinifaciens*; SEQ ID NOs:6/7). The *Saccharomyces cerevisiae* mevalonate kinase amino acid sequence (SEQ ID NO:1) is used as the reference for amino acid numbering to which the positions of the other sequences, e.g. the ones named above, are referred to (see also Table 3). Amino acids corresponding to positions 55, 59, 66, 83, 106, 111, 117, 142, 152, 158, 218, 231, 249, 367 and 375 of SEQ ID NO:1 are highlighted.

The following non-limiting examples further illustrate the invention.

EXAMPLE 1

Measurement of Mevalonate Kinase Activity and of Inhibition by Feedback Inhibitors For preparing mevalonate as substrate, 130 mg of DL-mevalonate lactone (FLUKA Chemie AG, Buchs, Switzerland) were dissolved in 5.5 ml of 0.2 M KOH and incubated for 15 min at 50° C. The solution was then adjusted to pH 7.0 by addition of 0.1 M HCl at room temperature (RT). Except if stated otherwise, the assay mixture consisted of 100 mM $K_2BPO/KH_2PO_4$ (pH 7.0), 1 mM ATP, 2 mM $MgCl_2$, 1 mM mevalonate, 0.5 mM phosphoenolpyruvate (PEP), 0.32 mM NADH, 20 U/ml pyruvate kinase and 27 U/ml lactate dehydrogenase (Sigma-Aldrich, St. Louis, Mo., USA). Inhibition was tested by adding 1 µM FPP.

Purification of $His_6$-tagged mevalonate kinase and of $His_6$-tagged mevalonate kinase mutant enzymes was done with Ni-NTA chromatography using the QIAexpress system/reagents of Qiagen. Upon addition of purified ($His_6$-tagged) mevalonate kinase, enzymatic reaction reflected by consumption of NADH was followed by photometric measurement at 340 nm. One unit (1 U) of mevalonate kinase activity catalyzes the phosphorylation of 1 µmol of mevalonate per min.

EXAMPLE 2

Generation of Feedback-resistant Mutants of *Saccharomyces cerevisiae* Mevalonate Kinase The cDNA of mevalonate kinase from *Saccharomyces cerevisiae* (SEQ ID NO:2) is amplified by PCR using primer Mvk-SphI containing an SphI restriction site (SEQ ID NO:10) along with a sequence of $His_6$ as well as a piece of the 5'-end sequence of mevalonate kinase without the ATG start codon, and primer Mvk-HindIII containing the 3'-end sequence of mevalonate kinase including the stop codon and a HindIII restriction site (SEQ ID NO:11). The PCR reaction is run according to the supplier's protocol (1 cycle at 94.5° C.

for 30 sec; 25 cycles at 94.5° C. for 30 sec, 55° C. for 30 sec, 70° C. for 3 min) using Turbo-Pfu polymerase of Stratagene (La Jolla, Calif., USA). After purification by agarose gel electrophoresis, the PCR product is digested by SphI and HindIII and ligated into pQE-80L (Qiagen, Hilden, Germany) digested with the same enzymes, resulting in pQE-80L-His$_6$-Mvk. Plasmid pQE-80L contains a T5 promoter regulated by a lac operator element, which can be cis-inhibited by the lac repressor also encoded by pQE-80L. The plasmid is then transformed into E. coli DH5α (Invitrogen, Carlsbad, Calif., USA) according to the supplier's protocol. Upon addition of 100 μM IPTG at an OD$_{600\ nm}$ of 0.6 during exponential growth of E. coli, His$_6$-tagged mevalonate kinase is induced at 30° C. for 4 h by shaking at 250 rpm.

Site-directed mutagenesis of His$_6$-tagged mevalonate kinase is achieved by the so-called "two step PCR" using Turbo-Pfu DNA polymerase of Stratagene (La Jolla, Calif., USA). The first PCR (see above for conditions) is performed with one of the primers represented by SEQ ID NOs:12-26 containing the mutated codons as the first primer and primer pQE-5' (SEQ ID NO:27) corresponding to a piece of sequence at the 5'-end of the multiple cloning sites (MCS) of pQE-80L as the second primer. The template is pQE-80L-His$_6$-Mvk. The PCR product is purified by agarose gel electrophoresis and used as a primer for the second PCR reaction together with the primer pQE-3' (SEQ ID NO:28) encompassing a piece of the 3'-end sequence of the MCS, with wild-type pQE-80L-His$_6$-Mvk as template. The PCR product (1.4 kb) is purified by agarose gel electrophoresis and digested by SphI and HindIII, with which the His$_6$-Mvk is subcloned into pQE-80L. Finally, the digested fragment is purified by agarose electrophoresis and ligated into pQE-80L linearized by the same restriction enzymes, resulting in a mutated pQE-80L-His$_6$-Mvk.

EXAMPLE 3

Feedback Resistance of Saccharomyces cerevisiae Mevalonate Kinase Mutants

Preparation of Mevalonate and Activity Measurement was Exactly Performed as Described in Example 1. 1 μM FPP was used for inhibition assays performed with the Saccharomyces cerevisiae mevalonate kinase wild-type enzyme and its mutants.

Feedback resistance (%) was calculated according to the following formula:

% resistance=100·((d/c)−(b/a))/(1−(b/a))

wherein (a) and (b) refer to the measured mevalonate kinase activities of the wild-type enzyme in the absence and presence, respectively, and (c) and (d) refer to the measured mevalonate kinase activities of the mutant enzyme in the absence and presence, respectively, of FPP. The results are shown in Tab. 1, wherein WT represents the non-mutated mevalonate kinase containing a His$_6$-tag (SEQ ID NO:3).

TABLE 1

Impact of mutagenesis of the Saccharomyces cerevisiae mevalonate kinase on the specific activity and the feedback resistance of the enzyme.

| Mutant | Specific activity (% of wild-type) | Feedback resistance (%) |
|---|---|---|
| WT | 100 | 0 |
| P55L, C117S | 60 | 58 |

TABLE 1-continued

Impact of mutagenesis of the Saccharomyces cerevisiae mevalonate kinase on the specific activity and the feedback resistance of the enzyme.

| Mutant | Specific activity (% of wild-type) | Feedback resistance (%) |
|---|---|---|
| F59S | 31 | 56 |
| N66K, I152M | 148 | 67 |
| K83E, S249P | 78 | 37 |
| H111N, K375N | 87 | 65 |
| L106P, S218P | 42 | 24 |
| I142N, L158S, L231I, T367S | 61 | 58 |

EXAMPLE 4

Saturated Mutagenesis of Saccharomyces cerevisiae Mevalonate Kinase at Amino Acid Residues/Positions Previously Identified to have an Impact on the Resistance of the Enzyme to Feedback Inhibition Saturated mutagenesis is done in the same way as described in Example 2, except that the mutagenesis primer is synthesized in a way that the codons subject to saturated mutagenesis are made of randomized sequence.

EXAMPLE 5

Improved Production of Coenzyme Q10 Using a Feedback Inhibition-resistant Mevalonate Kinase To test the in vivo effect of mutation N66K/I152M on the production of coenzyme Q10, the DNA encoding S. cerevisiae mevalonate kinase mutant N66K/I152M (SEQ ID NO:5) is introduced into Paracoccus zeaxanthinifaciens and compared to the CoQ10 production in P. zeaxanthinifaciens carrying the DNA encoding the wild-type S. cerevisiae mevalonate kinase (SEQ ID NO:2).

Plasmid Construction

The plasmid pQE-80L-His$_6$-Mvk (see Example 3) was introduced into E. coli according to Example 2. E. coli strains were grown at 37° C. in LB medium (Becton Dickinson, Sparks, Md., USA). For maintenance of plasmids in recombinant E. coli strains, ampicillin (100 μg/ml) and/or kanamycin (25-50 μg/ml, depending on the experiment) were added to the culture medium. Agar (1.5% final concentration) was added for solid media. Liquid cultures were grown in a rotary shaker at 200 rpm.

Plasmid pBBR-K-mev-op-R114 was constructed to contain the mevalonate operon, including its promoter region, from P. zeaxanthinifaciens R114, inserted between the SacI and NsiI sites of plasmid pBBR1MCS-2 (Kovach et al., Gene 166, 175-176, 1995). The cloned mevalonate operon corresponds to the sequence from nucleotides 2469 to 9001 of the sequence having the GenBank/EMBL accession number AJ431696. Between the SacI site and the mevalonate operon sequence there is a short linker sequence, which is derived from plasmid pCR®2.1-TOPO (Invitrogen, Carlsbad, Calif., USA) and corresponds to the sequence from the SacI site to the PCR fragment insertion site.

Introduction of a ddsA gene from P. zeaxanthinifaciens strain ATCC 21588 under the control of the crtE promoter region between the Ecl136H and the SpeI sites of pBBR-K-mev-op-R114 resulted in pBBR-K-mev-op-R114-PcrtE-ddsA$_{wt}$ (for construction of pBBR-K-PcrtE see Example 6 of WO 02/099095). The DNA sequence of the ddsa gene of strain ATCC 21588 (ddsA$_{wt}$) is shown in SEQ ID NO:29, the corresponding amino acid sequence is depicted as SEQ ID NO:30.

Plasmids according to pBBR-K-mev-op-R114-PcrtE-ddsA$_{wt}$, are constructed wherein the mevalonate operon, including its promoter region, from *P. zeaxanthinifaciens* R114 (see above) is replaced by either the DNA encoding the wild-type *S. cerevisiae* mevalonate kinase (SEQ ID NO:2) resulting in pBBR-K-mev-op-(*S. cerevisiae* mvk)-PcrtE-ddsA$_{wt}$ or the DNA encoding *S. cerevisiae* mevalonate kinase mutant N66K/I152M (SEQ ID NO:5) resulting in pBBR-K-mev-op-(*S. cerevisiae* mvk-N66K/I152M)-PcrtE-ddsA$_{wt}$.

Construction of Recombinant *P. zeaxanthinifaciens* Strains

*P. zeaxanthinifaciens* strains are grown at 28° C. The compositions of the media used for cultivation of *P. zeaxanthinifaciens* are described below. All liquid cultures of *P. zeaxanthinifaciens* grown in flasks are shaken in a rotary shaker at 200 rpm unless specified otherwise. Agar (2% final concentration) is added for solid medium. When media are sterilized by autoclaving, glucose is added (as a concentrated stock solution) after sterilization to achieve the desired final concentration. F-Medium contains (per liter distilled water): 10 g tryptone, 10 g yeast extract, 30 g NaCl, 10 g D-glucose.H$_2$O, 5 g MgSO$_4$.7H$_2$O. The pH is adjusted to 7.0 before sterilization by filtration or autoclaving. Medium 362F/2 contains (per liter distilled water): 33 g D-glucose.H$_2$O, 10 g yeast extract, 10 g tryptone, 5 g NaCl, 2.5 g MgSO$_4$.7H$_2$O. The pH of the medium is adjusted to 7.4 before sterilization by filtration or autoclaving. Following sterilization, 2.5 ml each (per liter of final solution) of microelements solution, NKP solution and CaFe solution are added. The latter three solutions are sterilized by filtration. Microelements solution contains (per liter distilled water): 80 g (NH$_4$)$_2$Fe(SO$_4$)$_2$.6H$_2$O, 6 g ZnSO$_4$.7H$_2$O, 2 g MnSO$_4$.H$_2$O, 0.2 g NiSO$_4$.6H$_2$O, 6 g EDTA. NKP solution contains (per liter distilled water): 250 g K$_2$BPO$_4$, 300 g (NH$_4$)$_2$PO$_4$. CaFe solution contains (per liter distilled water): 75 g CaCl$_2$.2H$_2$O, 5 g FeCl$_3$.6H$_2$O, 3.75 ml concentrated HCl.

Preparation of electrocompetent cells of *P. zeaxanthinifaciens* strain R114 and electroporation are performed as follows: 100 ml F-medium is inoculated with 1.5 ml of a stationary phase culture of *P. zeaxanthinifaciens* strain R114 and grown at 28° C., 200 rpm until an optical density at 660 nm of about 0.5 is reached. The cells are harvested by centrifugation for 15 minutes at 4° C., 7000×g and washed twice in 100 ml ice-cold HEPES buffer, pH 7. The final pellet is resuspended in 0.1 ml ice-cold HEPES buffer, pH 7 and the cells are either used immediately for electroporation or glycerol is added to a final concentration of 15% and the cells are stored in 50 μl aliquots at −80° C. One to five μl plasmid DNA is added in salt-free solution and electroporations are performed at 18 kV/cm and 129 Ohms in ice-cooled 1-mm cuvettes. Pulse lengths are typically between 4 and 5 milliseconds. One ml of F-medium is added and the cells are incubated for 1 hour at 28° C. Dilutions are spread onto F-agar plates containing 25-50 μg/ml kanamycin and incubated at 28° C. Putative transformants are confirmed to contain the desired plasmid by PCR analysis.

Culture Conditions for Evaluating Coenzyme Q10 Production

Coenzyme Q10 production is tested in fed-batch cultivations of *P. zeaxanthinifaciens* strains R114/pBBR-K-mev-opR114-PcrtE-ddsA$_{wt}$, R114/pBBR-K-mev-op-(*S. cerevisiae* mvk)-PcrtE-ddsA$_{wt}$ and R114/pBBR-K-mev-op-(*S. cerevisiae* mvk-N66K/I152M)-PcrtE-ddsA$_{wt}$. All cultures are initiated from frozen cell suspensions (stored as 25% glycerol stocks at −80° C.). The precultures for the fed-batch fermentations are prepared in duplicate 2-liter baffled shake flasks containing 200 ml of 362F/2 medium each. Two milliliters of thawed cell suspension are used as inoculum for each flask. The initial pH of the precultures is 7.2. The precultures are incubated at 28° C. with shaking at 250 rpm for 28 h, after which time the optical density at 660 nm (OD$_{660}$) is between 14 and 22 absorbance units, depending on the strain used. Main cultures are grown in Biostat ED Bioreactors (B. Braun Biotech International, Melsungen, Germany) containing medium having the following composition (per liter distilled water): 25 g D-glucose.H$_2$O, 17 g yeast extract (Tastone 900), 4.0 g NaCl, 6.25 g MgSO$_4$.7H$_2$O, 0.5 g (NH$_4$)$_2$Fe(SO$_4$)$_2$.6H$_2$O, 0.038 g ZnSO$_4$.7H$_2$O, 0.013 g MnSO$_4$.H$_2$O, 0.001 g NiSO$_4$.6H$_2$O, 0.47 g CaCl$_2$.2H$_2$O, 0.062 g FeCl$_3$.6H$_2$O, 0.01 g niacin, 0.5 g NH$_4$Cl, 0.1 ml antifoam, 3.5 ml KP solution. The composition of KP solution is (per liter distilled water): 250 g K$_2$HPO$_4$, 200 g NaH$_2$PO$_4$.2H$_2$O, 100 g (NH$_4$)$_2$HPO$_4$. Kanamycin (50 mg/l final concentration) is added to the medium for plasmid-carrying strains. The feeding solution used in all processes has the following composition (per liter distilled water): 550 g D-glucose.H$_2$O, 18.25 ml KP solution. The initial volume in the bioreactor (after inoculation) is 8.0 l. Precultures are diluted as needed with sterile water such that addition of 400 ml to the bioreactor results in an initial OD$_{660}$ value of 0.5. Fermentation conditions are automatically controlled as follows: 28° C., pH 7.2 (pH controlled with addition of 28% NH$_4$OH), dissolved oxygen controlled at a minimum of 40% relative value by agitation, minimum agitation of 300 rpm and an aeration rate of 1 v.v.m. (relative to final volume). The cultivations proceed under these conditions without addition of feed solution for about 20 h (batch phase) followed by the feeding phase. After this time, a decrease in agitation speed, cessation of base consumption, a sharp pH increase and a decrease in CO$_2$ production are the indication that the initial glucose is exhausted and the feeding is started. A standard feed profile is defined as follows (from feeding start point): ramp from 50 g/h to 80 g/h in 17 h, continue at 80 g/h for 7 b, then ramp down to 55 g/h in 11 h, and continue at 55 g/h for the rest of the fermentation (total fermentation time=70 h). The final volumes of the main cultures are about 10 liters.

Analytical Methods

400 μl of whole cultivation broth are transferred to a disposable 15 ml polypropylene centrifuge tube. Four milliliters of stabilized extraction solution (0.5 g/l 3,5-di-tert-butyl-4-hydroxytoluene) in 1:1 (v/v) (DMSO/tetrahydrofuran) are added and the samples are mixed for 20 min in a laboratory shaker (IKA, Germany) to enhance extraction. Finally, the samples are centrifuged and the supernatants transferred to amber glass vials for analysis by reverse phase HPLC. This method was developed for the simultaneous determination of ubiquinones and their corresponding hydroquinones, with a clear separation of CoQ10 from the carotenoids zeaxanthin, phytoene, β-cryptoxanthin, β-carotene and lycopene. Chromatography is performed using an Agilent 1100 HPLC system (Agilent Technologies, USA) equipped with a temperature-controlled autosampler and a diode array detector. The method parameters were as follows:

| Column | YMC Carotenoid C30 column<br>3 micron, steel, 150 mm × 3.0 mm I.D.<br>(YMC Europe GmbH, Dinslaken, Germany, Part No. CT99S031503QT) |
|---|---|

| | |
|---|---|
| Guard column | Security Guard C18 (ODS, Octadecyl) 4 mm length × 3.0 mm I.D. (Phenomenex, Torrance, CA, USA, Part No. AJO-4287) |
| Typical column pressure | 60 bar at start |
| Flow rate | 0.5 ml/min |
| Mobile phase | Mixture of acetonitrile(A):methanol(B):TBME(C) |
| Gradient profile | see below |

| Time (min) | % A | % B | % C |
|---|---|---|---|
| 0 | 60 | 15 | 25 |
| 13 | 60 | 15 | 25 |
| 20 | 0 | 0 | 100 |
| 22 | 60 | 15 | 25 |
| 25 | 60 | 15 | 25 |

| | |
|---|---|
| Post time | 4 min |
| Injection volume | 10 μl |
| Column temperature | 15° C. |
| Detection | Three wavelengths were used for detection of specific compounds according to Table 2. |

TABLE 2

HPLC retention times and wavelengths used

| Compound | Wavelength (nm) | Retention times (min) |
|---|---|---|
| Zeaxanthin (Z-isomers) | 450 | 4.2, 6.4 |
| E-Zeaxanthin | 450 | 5.2 |
| Phytoene | 280 | 7.7 |
| β-Cryptoxanthin | 450 | 8.6 |
| Ubiquinol 10 | 210 | 11.4 |
| Coenzyme Q10 | 210 | 12.8 |
| β-Carotene | 450 | 14.5 |
| Lycopene | 450 | 22.0 |

Calculations: Calculations are based on peak areas.

Coenzyme Q10 Production Results

Under the fed-batch cultivation conditions described above, the final concentration of coenzyme Q10 produced by *P. zeaxanthinifaciens* strain R114/pBBR-K-mev-op-(*S. cerevisiae* mvk-N66K/I152M)-PcrtE-ddsA$_{wt}$ is at least 5% higher than observed for strain R114 carrying plasmid pBBR-K-mev-op-(*S. cerevisiae* mvk)-PcrtE-ddsA$_{wt}$.

EXAMPLE 6

Identification of Corresponding Residues in Mevalonate Kinases that are Homologous to *Saccharomyces cerevisiae* Mevalonate Kinase A multiple amino acid sequence alignment of different mevalonate kinases was calculated as shown in FIG. 1. The sequence named as "Mvk_yeast" corresponds to SEQ ID NO:1, the sequence named as "Mvk-P-zeaxanthinifaciens" corresponds to SEQ ID NO:6.

The following residues corresponding to specific amino acid positions of the amino acid sequence of *Saccharomyces cerevisiae* mevalonate kinase (SEQ ID NO:1) were identified (for further reference to the source of Mvk, i.e. name of the organism, including accession numbers of the respective sequences see legend to FIG. 1):

TABLE 3

Amino acid residues from various organisms (see FIG. 1) corresponding to the positions 55, 59, 66, 83, 106, 111, 117, 142, 152, 158, 218, 231, 249, 367, 375 of *S. cerevisiae* mevalonate kinase (Yeast; SEQ ID NO: 1).

| Source of Mvk | Amino acid position | | | | | | | | | | | | | | |
|---|---|---|---|---|---|---|---|---|---|---|---|---|---|---|---|
| Yeast | P55 | F59 | N66 | K83 | L106 | H111 | C117 | I142 | I152 | L158 | S218 | L231 | S249 | T367 | K375 |
| Mouse | P54 | I58 | G65 | — | P98 | E105 | A111 | P139 | Y149 | A155 | — | L224 | S242 | E349 | K357 |
| Rat | P54 | I58 | A65 | — | P98 | E105 | A111 | P139 | Y149 | A155 | — | L224 | S242 | E349 | K357 |
| H-sapiens | P54 | I58 | A65 | — | P98 | E105 | A111 | P139 | Y149 | A155 | — | L224 | N242 | E349 | K357 |
| P_rhodozyma | T61 | F65 | D72 | — | G106 | E113 | A119 | M146 | L156 | L162 | — | I236 | D254 | S362 | M370 |
| S_pombe | S53 | T57 | Q64 | — | E98 | I103 | C109 | L134 | I144 | T150 | T211 | L221 | S239 | K343 | K351 |
| A_pernix | R44 | K45 | S52 | — | — | — | — | P104 | S114 | L120 | — | R176 | R194 | V295 | V303 |
| P_abyssi | E51 | I55 | V62 | — | A96 | — | — | V112 | V122 | G128 | — | H181 | S199 | — | V307 |
| P_horikoshii | E51 | I55 | V62 | — | S96 | — | — | V112 | V122 | G128 | — | P181 | S199 | — | V307 |
| P_furiosus | E49 | I53 | V60 | — | A94 | — | — | V111 | V121 | G127 | — | H180 | P198 | — | V306 |
| M_thermoautotr. | P49 | I53 | — | — | — | — | — | A91 | L101 | L107 | — | Q161 | E179 | — | V282 |
| A_fulgidus | — | I44 | — | — | R72 | — | — | I87 | V97 | A103 | — | E156 | S170 | — | — |
| M_jannaschii | N49 | K53 | N60 | — | L87 | — | — | I105 | I115 | K121 | — | E181 | K199 | — | — |
| P_zeaxanthinifac. | A57 | G61 | K68 | — | A102 | L109 | P115 | I143 | I153 | V159 | — | P210 | R228 | A340 | H348 |

The invention claimed is:

1. A modified mevalonate kinase comprising an amino acid sequence having at least 95% amino acid sequence identity to the amino acid sequence of SEQ ID NO:1, wherein the amino acid sequence of the modified mevalonate kinase contains one mutation or combination of mutations selected from the group consisting of:
   (1) combination of P55L and C117S mutations;
   (2) F59S mutation;
   (3) combination of N66K and I152M mutations;
   (4) combination of K83E and S249P mutations;
   (5) combination of H111N and K375N mutations;
   (6) combination of L106P and S218P mutations; and
   (7) combination of I142N, L158S, L231I and T367S mutations wherein the one mutation or combination of mutations of (1) to (7) corresponds to the amino acid sequence of SEQ ID NO: 1 and wherein the modified mevalonate kinase has mevalonate kinase activity and exhibits a sensitivity to feedback inhibition which is reduced by at least 20% in comparison to the corresponding non-modified *Saccharomyces cerevisiae* mevalonate kinase as shown in SEQ ID NO: 1.

* * * * *

SEQUENCE LISTING

<160> NUMBER OF SEQ ID NOS: 41

<210> SEQ ID NO 1
<211> LENGTH: 443
<212> TYPE: PRT
<213> ORGANISM: Saccharomyces cerevisiae

<400> SEQUENCE: 1

Met Ser Leu Pro Phe Leu Thr Ser Ala Pro Gly Lys Val Ile Ile Phe
1               5                   10                  15

```
Gly Glu His Ser Ala Val Tyr Asn Lys Pro Ala Val Ala Ser Val
            20                  25                  30

Ser Ala Leu Arg Thr Tyr Leu Leu Ile Ser Glu Ser Ser Ala Pro Asp
            35                  40                  45

Thr Ile Glu Leu Asp Phe Pro Asp Ile Ser Phe Asn His Lys Trp Ser
            50                  55                  60

Ile Asn Asp Phe Asn Ala Ile Thr Glu Asp Gln Val Asn Ser Gln Lys
65                  70                  75                  80

Leu Ala Lys Ala Gln Gln Ala Thr Asp Gly Leu Ser Gln Glu Leu Val
                85                  90                  95

Ser Leu Leu Asp Pro Leu Leu Ala Gln Leu Ser Glu Ser Phe His Tyr
            100                 105                 110

His Ala Ala Phe Cys Phe Leu Tyr Met Phe Val Cys Leu Cys Pro His
            115                 120                 125

Ala Lys Asn Ile Lys Phe Ser Leu Lys Ser Thr Leu Pro Ile Gly Ala
            130                 135                 140

Gly Leu Gly Ser Ser Ala Ser Ile Ser Val Ser Leu Ala Leu Ala Met
145                 150                 155                 160

Ala Tyr Leu Gly Gly Leu Ile Gly Ser Asn Asp Leu Glu Lys Leu Ser
                165                 170                 175

Glu Asn Asp Lys His Ile Val Asn Gln Trp Ala Phe Ile Gly Glu Lys
            180                 185                 190

Cys Ile His Gly Thr Pro Ser Gly Ile Asp Asn Ala Val Ala Thr Tyr
            195                 200                 205

Gly Asn Ala Leu Leu Phe Glu Lys Asp Ser His Asn Gly Thr Ile Asn
            210                 215                 220

Thr Asn Asn Phe Lys Phe Leu Asp Asp Phe Pro Ala Ile Pro Met Ile
225                 230                 235                 240

Leu Thr Tyr Thr Arg Ile Pro Arg Ser Thr Lys Asp Leu Val Ala Arg
                245                 250                 255

Val Arg Val Leu Val Thr Glu Lys Phe Pro Glu Val Met Lys Pro Ile
            260                 265                 270

Leu Asp Ala Met Gly Glu Cys Ala Leu Gln Gly Leu Glu Ile Met Thr
            275                 280                 285

Lys Leu Ser Lys Cys Lys Gly Thr Asp Glu Ala Val Glu Thr Asn
            290                 295                 300

Asn Glu Leu Tyr Glu Gln Leu Glu Leu Ile Arg Ile Asn His Gly
305                 310                 315                 320

Leu Leu Val Ser Ile Gly Val Ser His Pro Gly Leu Glu Leu Ile Lys
                325                 330                 335

Asn Leu Ser Asp Asp Leu Arg Ile Gly Ser Thr Lys Leu Thr Gly Ala
            340                 345                 350

Gly Gly Gly Gly Cys Ser Leu Thr Leu Arg Arg Asp Ile Thr Gln
            355                 360                 365

Glu Gln Ile Asp Ser Phe Lys Lys Lys Leu Gln Asp Asp Phe Ser Tyr
            370                 375                 380

Glu Thr Phe Glu Thr Asp Leu Gly Gly Thr Gly Cys Cys Leu Leu Ser
385                 390                 395                 400

Ala Lys Asn Leu Asn Lys Asp Leu Lys Ile Lys Ser Leu Val Phe Gln
                405                 410                 415

Leu Phe Glu Asn Lys Thr Thr Thr Lys Gln Gln Ile Asp Asp Leu Leu
            420                 425                 430

Leu Pro Gly Asn Thr Asn Leu Pro Trp Thr Ser
```

-continued

<210> SEQ ID NO 2
<211> LENGTH: 1332
<212> TYPE: DNA
<213> ORGANISM: Saccharomyces cerevisiae

<400> SEQUENCE: 2

```
atgtcattac cgttcttaac ttctgcaccg ggaaaggtta ttattttttgg tgaacactct      60
gctgtgtaca acaagcctgc cgtcgctgct agtgtgtctg cgttgagaac ctacctgcta     120
ataagcgagt catctgcacc agatactatt gaattggact ccccggacat tagctttaat     180
cataagtggt ccatcaatga tttcaatgcc atcaccgagg atcaagtaaa ctcccaaaaa     240
ttggccaagg ctcaacaagc caccgatggc ttgtctcagg aactcgttag tcttttggat     300
ccgttgttag ctcaactatc cgaatccttc cactaccatg cagcgttttg tttcctgtat     360
atgtttgttt gcctatgccc ccatgccaag aatattaagt tttcttttaaa gtctacttta     420
cccatcggtg ctgggttggg ctcaagcgcc tctatttctg tatcactggc cttagctatg     480
gcctacttgg gggggttaat aggatctaat gacttggaaa agctgtcaga aaacgataag     540
catatagtga atcaatgggc cttcataggt gaaaagtgta ttcacggtac cccttcagga     600
atagataacg ctgtggccac ttatggtaat gccctgctat ttgaaaaaga ctcacataat     660
ggaacaataa acacaaacaa tttaagttc ttagatgatt cccagccat tccaatgatc     720
ctaacctata ctagaattcc aaggtctaca aaagatcttg ttgctcgcgt tcgtgtgttg     780
gtcaccgaga atttcctga gttatgaag ccaattctag atgccatggg tgaatgtgcc     840
ctacaaggct tagagatcat gactaagtta agtaaatgta aaggcaccga tgacgaggct     900
gtagaaacta ataatgaact gtatgaacaa ctattggaat tgataagaat aaatcatgga     960
ctgcttgtct caatcggtgt ttctcatcct ggattagaac ttattaaaaa tctgagcgat    1020
gatttgagaa ttggctccac aaaacttacc ggtgctggtg gcggcggttg ctctttgact    1080
ttgttacgaa gagacattac tcaagagcaa attgacagct tcaaaaagaa attgcaagat    1140
gattttagtt acgagacatt tgaaacagac ttgggtggga ctggctgctg tttgttaagc    1200
gcaaaaaatt tgaataaaga tcttaaaatc aaatccctag tattccaatt atttgaaaat    1260
aaaactacca caaagcaaca aattgacgat ctattattgc caggaaacac gaatttacca    1320
tggacttcat aa                                                         1332
```

<210> SEQ ID NO 3
<211> LENGTH: 456
<212> TYPE: PRT
<213> ORGANISM: Artificial sequence
<220> FEATURE:
<223> OTHER INFORMATION: Saccharomyces cerevisiae

<400> SEQUENCE: 3

```
Met Arg Gly Ser His His His His His His Gly Ser Ala Cys Ser Leu
1               5                   10                  15

Pro Phe Leu Thr Ser Ala Pro Gly Lys Val Ile Ile Phe Gly Glu His
            20                  25                  30

Ser Ala Val Tyr Asn Lys Pro Ala Val Ala Ala Ser Val Ser Ala Leu
        35                  40                  45

Arg Thr Tyr Leu Leu Ile Ser Glu Ser Ser Ala Pro Asp Thr Ile Glu
    50                  55                  60

Leu Asp Phe Pro Asp Ile Ser Phe Asn His Lys Trp Ser Ile Asn Asp
65                  70                  75                  80
```

Phe Asn Ala Ile Thr Glu Asp Gln Val Asn Ser Gln Lys Leu Ala Lys
                85                  90                  95

Ala Gln Gln Ala Thr Asp Gly Leu Ser Gln Glu Leu Val Ser Leu Leu
            100                 105                 110

Asp Pro Leu Leu Ala Gln Leu Ser Glu Ser Phe His Tyr His Ala Ala
        115                 120                 125

Phe Cys Phe Leu Tyr Met Phe Val Cys Leu Cys Pro His Ala Lys Asn
    130                 135                 140

Ile Lys Phe Ser Leu Lys Ser Thr Leu Pro Ile Gly Ala Gly Leu Gly
145                 150                 155                 160

Ser Ser Ala Ser Ile Ser Val Ser Leu Ala Leu Ala Met Ala Tyr Leu
                165                 170                 175

Gly Gly Leu Ile Gly Ser Asn Asp Leu Glu Lys Leu Ser Glu Asn Asp
            180                 185                 190

Lys His Ile Val Asn Gln Trp Ala Phe Ile Gly Glu Lys Cys Ile His
        195                 200                 205

Gly Thr Pro Ser Gly Ile Asp Asn Ala Val Ala Thr Tyr Gly Asn Ala
    210                 215                 220

Leu Leu Phe Glu Lys Asp Ser His Asn Gly Thr Ile Asn Thr Asn Asn
225                 230                 235                 240

Phe Lys Phe Leu Asp Asp Phe Pro Ala Ile Pro Met Ile Leu Thr Tyr
                245                 250                 255

Thr Arg Ile Pro Arg Ser Thr Lys Asp Leu Val Ala Arg Val Arg Val
            260                 265                 270

Leu Val Thr Glu Lys Phe Pro Glu Val Met Lys Pro Ile Leu Asp Ala
        275                 280                 285

Met Gly Glu Cys Ala Leu Gln Gly Leu Glu Ile Met Thr Lys Leu Ser
    290                 295                 300

Lys Cys Lys Gly Thr Asp Asp Glu Ala Val Glu Thr Asn Asn Glu Leu
305                 310                 315                 320

Tyr Glu Gln Leu Leu Glu Leu Ile Arg Ile Asn His Gly Leu Leu Val
                325                 330                 335

Ser Ile Gly Val Ser His Pro Gly Leu Glu Leu Ile Lys Asn Leu Ser
            340                 345                 350

Asp Asp Leu Arg Ile Gly Ser Thr Lys Leu Thr Gly Ala Gly Gly Gly
        355                 360                 365

Gly Cys Ser Leu Thr Leu Leu Arg Arg Asp Ile Thr Gln Glu Gln Ile
    370                 375                 380

Asp Ser Phe Lys Lys Lys Leu Gln Asp Phe Ser Tyr Glu Thr Phe
385                 390                 395                 400

Glu Thr Asp Leu Gly Gly Thr Gly Cys Cys Leu Leu Ser Ala Lys Asn
                405                 410                 415

Leu Asn Lys Asp Leu Lys Ile Lys Ser Leu Val Phe Gln Leu Phe Glu
            420                 425                 430

Asn Lys Thr Thr Thr Lys Gln Gln Ile Asp Asp Leu Leu Leu Pro Gly
        435                 440                 445

Asn Thr Asn Leu Pro Trp Thr Ser
    450                 455

<210> SEQ ID NO 4
<211> LENGTH: 1371
<212> TYPE: DNA
<213> ORGANISM: Artificial sequence
<220> FEATURE:
<223> OTHER INFORMATION: Saccharomyces cerevisiae

```
<400> SEQUENCE: 4
atgagaggat cgcatcacca tcaccatcac ggatccgcat gctcattacc gttcttaact    60
tctgcaccgg gaaaggttat tattttggt gaacactctg ctgtgtacaa caagcctgcc    120
gtcgctgcta gtgtgtctgc gttgagaacc tacctgctaa taagcgagtc atctgcacca    180
gatactattg aattggactt cccggacatt agctttaatc ataagtggtc catcaatgat    240
ttcaatgcca tcaccgagga tcaagtaaac tcccaaaaat tggccaaggc tcaacaagcc    300
accgatggct tgtctcagga actcgttagt cttttggatc cgttgttagc tcaactatcc    360
gaatccttcc actaccatgc agcgttttgt ttcctgtata tgtttgtttg cctatgcccc    420
catgccaaga atattaagtt ttcttaaag tctactttac ccatcggtgc tgggttgggc    480
tcaagcgcct ctatttctgt atcactggcc ttagctatgg cctacttggg ggggttaata    540
ggatctaatg acttggaaaa gctgtcagaa acgataagc atatagtgaa tcaatgggcc    600
ttcataggtg aaaagtgtat tcacggtacc ccttcaggaa tagataacgc tgtggccact    660
tatggtaatg ccctgctatt tgaaaaagac tcacataatg aacaataaa cacaaacaat    720 tttaagttct tagatgattt cccagccatt ccaatgatcc taacctatac tagaattcca    780
aggtctacaa agatcttgt tgctcgcgtt cgtgtgttgg tcaccgagaa atttcctgaa    840
gttatgaagc caattctaga tgccatgggt gaatgtgccc tacaaggctt agagatcatg    900
actaagttaa gtaaatgtaa aggcaccgat gacgaggctg tagaaactaa taatgaactg    960
tatgaacaac tattggaatt gataagaata aatcatggac tgcttgtctc aatcggtgtt    1020
tctcatcctg gattagaact tattaaaaat ctgagcgatg atttgagaat tggctccaca    1080
aaacttaccg gtgctggtgg cggcggttgc tctttgactt tgttacgaag agacattact    1140
caagagcaaa ttgacagctt caaaagaaa ttgcaagatg atttagtta cgagacattt    1200 gaaacagact gggtgggac tggctgctgt ttgttaagcg caaaaatt gaataaagat    1260 cttaaaatca aatccctagt attccaatta tttgaaaata aaactaccac aaagcaacaa    1320
attgacgatc tattattgcc aggaaacacg aatttaccat ggacttcata a              1371

<210> SEQ ID NO 5
<211> LENGTH: 1371
<212> TYPE: DNA
<213> ORGANISM: Artificial sequence
<220> FEATURE:
<223> OTHER INFORMATION: Saccharomyces cerevisiae N66K, I152M

<400> SEQUENCE: 5
atgagaggat cgcatcacca tcaccatcac ggatccgcat gctcattacc gttcttaact    60
tctgcaccgg gaaaggttat tattttggt gaacactctg ctgtgtacaa caagcctgcc    120
gtcgctgcta gtgtgtctgc gttgagaacc tacctgctaa taagcgagtc atctgcacca    180
gatactattg aattggactt cccggacatt agctttaatc ataagtggtc catcaaagat    240
ttcaatgcca tcaccgagga tcaagtaaac tcccaaaaat tggccaaggc tcaacaagcc    300
accgatggct tgtctcagga actcgttagt cttttggatc cgttgttagc tcaactatcc    360
gaatccttcc actaccatgc agcgttttgt ttcctgtata tgtttgtttg cctatgcccc    420
catgccaaga atattaagtt ttcttaaag tctactttac ccatcggtgc tgggttgggc    480
tcaagcgcct ctatgtctgt atcactggcc ttagctatgg cctacttggg ggggttaata    540
ggatctaatg acttggaaaa gctgtcagaa acgataagc atatagtgaa tcaatgggcc    600
ttcataggtg aaaagtgtat tcacggtacc ccttcaggaa tagataacgc tgtggccact    660
```

-continued

```
tatggtaatg ccctgctatt tgaaaaagac tcacataatg aacaataaa cacaaacaat    720
tttaagttct tagatgattt cccagccatt ccaatgatcc taacctatac tagaattcca    780
aggtctacaa aagatcttgt tgctcgcgtt cgtgtgttgg tcaccgagaa atttcctgaa    840
gttatgaagc caattctaga tgccatgggt gaatgtgccc tacaaggctt agagatcatg    900
actaagttaa gtaaatgtaa aggcaccgat gacgaggctg tagaaactaa taatgaactg    960
tatgaacaac tattggaatt gataagaata aatcatggac tgcttgtctc aatcggtgtt   1020
tctcatcctg gattagaact tattaaaaat ctgagcgatg atttgagaat tggctccaca   1080
aaacttaccg gtgctggtgg cggcggttgc tctttgactt tgttacgaag agacattact   1140
caagagcaaa ttgacagctt caaaaagaaa ttgcaagatg attttagtta cgagacattt   1200
gaaacagact tgggtgggac tggctgctgt ttgttaagcg caaaaaattt gaataaagat   1260
cttaaaatca aatccctagt attccaatta tttgaaaata aaactaccac aaagcaacaa   1320
attgacgatc tattattgcc aggaaacacg aatttaccat ggacttcata a           1371
```

<210> SEQ ID NO 6
<211> LENGTH: 378
<212> TYPE: PRT
<213> ORGANISM: Paracoccus zeaxanthinifaciens

<400> SEQUENCE: 6

```
Met Ser Thr Gly Arg Pro Glu Ala Gly Ala His Ala Pro Gly Lys Leu
1               5                   10                  15

Ile Leu Ser Gly Glu His Ser Val Leu Tyr Gly Ala Pro Ala Leu Ala
            20                  25                  30

Met Ala Ile Ala Arg Tyr Thr Glu Val Trp Phe Thr Pro Leu Gly Ile
        35                  40                  45

Gly Glu Gly Ile Arg Thr Thr Phe Ala Asn Leu Ser Gly Gly Ala Thr
    50                  55                  60

Tyr Ser Leu Lys Leu Leu Ser Gly Phe Lys Ser Arg Leu Asp Arg Arg
65                  70                  75                  80

Phe Glu Gln Phe Leu Asn Gly Asp Leu Lys Val His Lys Val Leu Thr
                85                  90                  95

His Pro Asp Asp Leu Ala Val Tyr Ala Leu Ala Ser Leu Leu His Asp
            100                 105                 110

Lys Pro Pro Gly Thr Ala Ala Met Pro Gly Ile Gly Ala Met His His
        115                 120                 125

Leu Pro Arg Pro Gly Glu Leu Gly Ser Arg Thr Glu Leu Pro Ile Gly
    130                 135                 140

Ala Gly Met Gly Ser Ser Ala Ala Ile Val Ala Thr Thr Val Leu
145                 150                 155                 160

Phe Glu Thr Leu Leu Asp Arg Pro Lys Thr Pro Glu Gln Arg Phe Asp
                165                 170                 175

Arg Val Arg Phe Cys Glu Arg Leu Lys His Gly Lys Ala Gly Pro Ile
            180                 185                 190

Asp Ala Ala Ser Val Val Arg Gly Gly Leu Val Arg Val Gly Gly Asn
        195                 200                 205

Gly Pro Gly Ser Ile Ser Ser Phe Asp Leu Pro Glu Asp His Asp Leu
    210                 215                 220

Val Ala Gly Arg Gly Trp Tyr Trp Val Leu His Gly Arg Pro Val Ser
225                 230                 235                 240

Gly Thr Gly Glu Cys Val Ser Ala Val Ala Ala His Gly Arg Asp
                245                 250                 255
```

```
Ala Ala Leu Trp Asp Ala Phe Ala Val Cys Thr Arg Ala Leu Glu Ala
            260                 265                 270

Ala Leu Leu Ser Gly Gly Ser Pro Asp Ala Ala Ile Thr Glu Asn Gln
        275                 280                 285

Arg Leu Leu Glu Arg Ile Gly Val Val Pro Ala Ala Thr Gln Ala Leu
    290                 295                 300

Val Ala Gln Ile Glu Glu Ala Gly Ala Ala Lys Ile Cys Gly Ala
305                 310                 315                 320

Gly Ser Val Arg Gly Asp His Gly Gly Ala Val Leu Val Arg Ile Asp
                325                 330                 335

Asp Ala Gln Ala Met Ala Ser Val Met Ala Arg His Pro Asp Leu Asp
                340                 345                 350

Trp Ala Pro Leu Arg Met Ser Arg Thr Gly Ala Ala Pro Gly Pro Ala
            355                 360                 365

Pro Arg Ala Gln Pro Leu Pro Gly Gln Gly
        370                 375
```

<210> SEQ ID NO 7
<211> LENGTH: 1137
<212> TYPE: DNA
<213> ORGANISM: Paracoccus zeaxanthinifaciens

<400> SEQUENCE: 7

```
atgtcgaccg gcaggcctga agcaggcgcc catgccccgg gcaagctgat cctgtccggg    60
gaacattccg tgctctatgg tgcgcccgcg cttgccatgg ccatcgcccg ctataccgag   120
gtgtggttca cgccgcttgg cattggcgag gggatacgca cgacattcgc caatctctcg   180
ggcggggcga cctattcgct gaagctgctg tcggggttca agtcgcggct ggaccgccgg   240
ttcgagcagt tcctgaacgg cgacctaaag gtgcacaagg tcctgaccca tcccgacgat   300
ctggcggtct atgcgctggc gtcgcttctg cacgacaagc cgccggggac cgccgcgatg   360
ccgggcatcg gcgcgatgca ccacctgccg cgaccgggtg agctgggcag ccggacggag   420
ctgcccatcg gcgcgggcat ggggtcgtct gcggccatcg tcgcggccac cacggtcctg   480
ttcgagacgc tgctggaccg gcccaagacg cccgaacagc gcttcgaccg cgtccgcttc   540
tgcgagcggt tgaagcacgg caaggccggt cccatcgacg cggccagcgt cgtgcgcggc   600
gggcttgtcc gcgtgggcgg gaacgggccg ggttcgatca gcagcttcga tttgcccgag   660
gatcacgacc ttgtcgcggg acgcggctgg tactgggtac tgcacgggcg ccccgtcagc   720
gggaccggcg aatgcgtcag cgcggtcgcg gcggcgcatg gtcgcgatgc ggcgctgtgg   780
gacgccttcg cagtctgcac ccgcgcgttg gaggccgcgc tgctgtctgg ggcagcccc   840
gacgccgcca tcaccgagaa ccagcgcctg ctggaacgca tcggcgtcgt gccggcagcg   900
acgcaggccc tcgtgcccca gatcgaggag gcgggtggcg cggccaagat ctgcggcgca   960
ggttccgtgc ggggcgatca cggcggggcg gtcctcgtgc ggattgacga cgcgcaggcg  1020
atggcttcgg tcatggcgcg ccatcccgac ctcgactggg cgcccctgcg catgtcgcgc  1080
acggggggcg cacccggccc cgcgccgcgt gcgcaaccgc tgccggggca gggctga     1137
```

<210> SEQ ID NO 8
<211> LENGTH: 432
<212> TYPE: PRT
<213> ORGANISM: Phaffia rhodozyma ATCC 96594

<400> SEQUENCE: 8

Lys Glu Glu Ile Leu Val Ser Ala Pro Gly Lys Val Ile Leu Phe Gly

-continued

```
1               5                   10                  15
Glu His Ala Val Gly His Gly Val Thr Gly Ile Ala Ala Ser Val Asp
                20                  25                  30

Leu Arg Cys Tyr Ala Leu Leu Ser Pro Thr Ala Thr Thr Thr Thr Ser
                35                  40                  45

Ser Ser Leu Ser Ser Thr Asn Ile Thr Ile Ser Leu Thr Asp Leu Asn
    50                  55                  60

Phe Thr Gln Ser Trp Pro Val Asp Ser Leu Pro Trp Ser Leu Ala Pro
65                  70                  75                  80

Asp Trp Thr Glu Ala Ser Ile Pro Glu Ser Leu Cys Pro Thr Leu Leu
                85                  90                  95

Ala Glu Ile Glu Arg Ile Ala Gly Gln Gly Gly Asn Gly Gly Glu Arg
                100                 105                 110

Glu Lys Val Ala Thr Met Ala Phe Leu Tyr Leu Val Leu Leu Leu Ser
                115                 120                 125

Lys Gly Lys Pro Ser Glu Pro Phe Glu Leu Thr Ala Arg Ser Ala Leu
    130                 135                 140

Pro Met Gly Ala Gly Leu Gly Ser Ser Ala Ala Leu Ser Thr Ser Leu
145                 150                 155                 160

Ala Leu Val Phe Leu Leu His Phe Ser His Leu Ser Pro Thr Thr Thr
                165                 170                 175

Gly Arg Glu Ser Thr Ile Pro Thr Ala Asp Thr Glu Val Ile Asp Lys
                180                 185                 190

Trp Ala Phe Leu Ala Glu Lys Val Ile His Gly Asn Pro Ser Gly Ile
                195                 200                 205

Asp Asn Ala Val Ser Thr Arg Gly Gly Ala Val Ala Phe Lys Arg Lys
    210                 215                 220

Ile Glu Gly Lys Gln Glu Gly Gly Met Glu Ala Ile Lys Ser Phe Thr
225                 230                 235                 240

Ser Ile Arg Phe Leu Ile Thr Asp Ser Arg Ile Gly Asp Thr Arg
                245                 250                 255

Ser Leu Val Ala Gly Val Asn Ala Arg Leu Ile Gln Glu Pro Glu Val
                260                 265                 270

Ile Val Pro Leu Leu Glu Ala Ile Gln Gln Ile Ala Asp Glu Ala Ile
                275                 280                 285

Arg Cys Leu Lys Asp Ser Glu Met Glu Arg Ala Val Met Ile Asp Arg
                290                 295                 300

Leu Gln Asn Leu Val Ser Glu Asn His Ala His Leu Ala Ala Leu Gly
305                 310                 315                 320

Val Ser His Pro Ser Leu Glu Glu Ile Ile Arg Ile Gly Ala Asp Lys
                325                 330                 335

Pro Phe Glu Leu Arg Thr Lys Leu Thr Gly Ala Gly Gly Gly Gly Cys
                340                 345                 350

Ala Val Thr Leu Val Pro Asp Asp Phe Ser Thr Glu Thr Leu Gln Ala
                355                 360                 365

Leu Met Glu Thr Leu Val Gln Ser Ser Phe Ala Pro Tyr Ile Ala Arg
                370                 375                 380

Val Gly Gly Ser Gly Val Gly Phe Leu Ser Ser Thr Lys Ala Asp Pro
385                 390                 395                 400

Glu Asp Gly Glu Asn Arg Leu Lys Asp Gly Leu Val Gly Thr Glu Ile
                405                 410                 415

Asp Glu Leu Asp Arg Trp Ala Leu Lys Thr Gly Arg Trp Ser Phe Ala
                420                 425                 430
```

<210> SEQ ID NO 9
<211> LENGTH: 4135
<212> TYPE: DNA
<213> ORGANISM: Phaffia rhodozyma ATCC 96594

<400> SEQUENCE: 9

```
actgactcgg ctaccggaaa atatcttttc aggacgcctt gatcgttttg gacaacacca      60
tgatgtcacc atatcttcag cggccgttgg agctaggagt agacattgta tacgactctg     120
gaacaaagta tttgagtgga caccacgatc tcatggctgg tgtgattact actcgtactg     180
aggagattgg gaaggttcgt gcttgcttgc tttgaatgtc gtgcctaaag ccattgccat     240
aagacagagt ctgatctatg tcgtttgcct acaacagaga atggcctggt tcccaaatgc     300
tatgggaaat gcattgtctc cgttcgactc gttccttctt ctccgaggac tcaaaacact     360
tcctctccga ctggacaagc agcaggcctc atctcacctg atcgcctcgt acttacacac     420
cctcggcttt cttgttcact accccggtct gccttctgac cctgggtacg aacttcataa     480
ctctcaggcg agtggtgcag gtgccgtcat gagctttgag accggagata tcgcgttgag     540
tgaggccatc gtgggcggaa cccgagtttg gggaatcagt gtcagtttcg gagccgtgaa     600
cagtttgatc agcatgcctt gtctaatgag gttagttctt atgccttctt ttcgcgcctt     660
ctaaaatttc tggctgacta attgggtcgg tcttttccgtt cttgcatttc agtcacgcat     720
ctattcctgc tcaccttcga gccgagcgag gtctccccga acatctgatt cgactgtgtg     780
tcggtattga ggaccctcac gatttgcttg atgatttgga ggcctctctt gtgaacgctg     840
gcgcaatccg atcagtctct acctcagatt catcccgacc gctcactcct cctgcctctg     900
attctgcctc ggacattcac tccaactggg ccgtcgaccg agccagacag ttcgagcgtg     960
ttaggccttc taactcgaca gccggcgtcg aaggacagct tgccgaactc aatgtagacg    1020
atgcagccag acttgcgggc gatgagagcc aaaaagaaga aattcttgtc agtgcaccgg    1080
gaaaggtcat tctgttcggc gaacatgctg taggccatgg tgttgtgagt gagaaatgaa    1140
agctttatgc tctcattgca tcttaacttt tcctcgcctt ttttgttctc ttcatcccgt    1200
cttgattgta gggatgcccc cctttgcccc tttccccttc ttgcatctgt ctatatttcc    1260
ttatacattt cgctcttaag agcgtctagt tgtaccttat aacaaccttt ggttttagca    1320
tcctttgatt attcatttct ctcatccttc ggtcagaggc tttcggccat ctttacgtct    1380
gattagattg taatagcaag aactatcttg ctaagccttt tctcttcctc ttcctcctat    1440
ataaatcgaa ttcactttcg gacatgttta ttttggggaa atcatcaagg ggtgggggc    1500
caatcccgac actaattttc tgctcacgtc aaaactcagc gttcagaatc agtcactgac    1560
cctgatacgt gtctctatgt gtgtgggtgt acgtgcgaat tgtgactcga cgttctacgc    1620
ttaaaaacag accgggatcg ctgcttccgt tgatcttcga tgctacgctc ttctctcacc    1680
cactgctacg acaacaacat catcgtcgtt atcgtctaca acattacca tctcccctaac    1740
ggacctgaac tttacgcagt cttggcctgt tgattctctt ccttggtcac ttgcgcctga    1800
ctggactgag gcgtctattc cagaatctct ctgcccgaca ttgctcgccg aaatcgaaag    1860
gatcgctggt caaggtggaa acggaggaga aagggagaag gtggcaacca tggcattctt    1920
gtatttgttg gtgctattga gcaaagggaa gccaaggtag gttttttctg tctcttcttt    1980
ttgcctataa agactcttaa ctgacggaga aagtgttggg tttcttcctt cgggggttca    2040
atcaattaaa gtgagccgtt cgagttgacg gctcgatctg cgcttccgat gggagctggt    2100
ctgggttcat ccgccgctct atcgacctct cttgccctag tctttcttct ccacttttct    2160
```

-continued

```
cacctcagtc caacgacgac tggcagagaa tcaacaatcc cgacggccga cacagaagta    2220
attgacaaat gggcgttctt agctgaaaaa gtcatccatg gaaatccgag tgggattgat    2280
aacgcggtca gtacgagagg aggcgctgtt gctttcaaaa gaaagattga gggaaaacag    2340
gaaggtggaa tggaagcgat caagaggtac gcagacacgg tgcttcatat gccatactcc    2400
agtctgattg acccatgatg aacgtctttc tacatttcga atatagcttc acatccattc    2460
gattcctcat cacagattct cgtatccgaa gggatacaag atctctcgtt gcaggagtga    2520
atgctcgact gattcaggag ccagaggtga tcgtcccttt gttggaagcg attcagcaga    2580
ttgccgatga ggctattcga tgcttgaaag attcagagat ggaacgtgct gtcatgatcg    2640
atcgacttca agttagttct tgttcctttc aagactcttt gtgacattgt gtcttatcca    2700
tttcatcttc ttttttcttc cttcttctgc agaacttggt ctccgagaac cacgcacacc    2760
tagcagcact tggcgtgtcc cacccatccc tcgaagagat tatccggatc ggtgctgata    2820
agcctttcga gcttcgaaca agttgacag gcgccggtgg aggtggttgc gctgtaaccc    2880
tggtgcccga tggtaaagtc tctccttttc tcttccgtcc aagcgacaca tctgaccgat    2940
gcgcatcctg tacttttggt caaccagact tctcgactga aacccttcaa gctcttatgg    3000
agacgctcgt tcaatcatcg ttcgcccctt atattgcccg agtgggtggt tcaggcgtcg    3060
gattcctttc atcaactaag gccgatccgg aagatgggga aacagactt aaagatgggc    3120 tggtgggaac ggagattgat gagctagaca gatgggcttt gaaaacgggt cgttggtctt    3180
ttgcttgaac gaaagatagg aaacggtgat tagggtacag atcctttgct gtcattttta    3240
caaaacactt tcttatgtct tcatgactca acgtatgccc tcatctctat ccatagacag    3300
cacggtacct ctcaggtttc aatacgtaag cgttcatcga caaacatgc ggcacacgaa    3360 aacgagtgga tataagggag aagagagata ttagagcgaa aaagagaaga gtgagagagg    3420
aaaaaaataa ccgagaacaa cttattccgg tttgttagaa tcgaagatcg agaaatatga    3480
agtacatagt ataaagtaaa gaagagaggt ttacctcaga ggtgtgtacg aaggtgagga    3540
caggtaagag gaataattga ctatcgaaaa aagagaactc aacagaagca ctgggataaa    3600
gcctagaatg taagtctcat cggtccgcga tgaaagagaa attgaaggaa gaaaaagccc    3660
ccagtaaaca atccaaccaa cctcttggac gattgcgaaa cacacacacg cacgcggaca    3720
tatttcgtac acaaggacgg gacattcttt ttatatcc gggtgggag agagagggtt    3780 atagaggatg aatagcaagg ttgatgtttt gtaaaaggtt gcagaaaaag gaaagtgaga    3840
gtaggaacat gcattaaaaa cctgcccaaa gcgatttata tcgttcttct gttttcactt    3900 cttttccgggc gctttcttag accgcggtgg tgaagggtta ctcctgccaa ctagaagaag    3960
caacatgagt caaggattag atcatcacgt gtctcatttg acgggttgaa agatatattt    4020
agatactaac tgcttcccac gccgactgaa aagatgaatt gaatcatgtc gagtggcaac    4080
gaacgaaaga acaaatagta agaatgaatt actagaaaag acagaatgac tagaa         4135
```

<210> SEQ ID NO 10
<211> LENGTH: 29
<212> TYPE: DNA
<213> ORGANISM: Artificial sequence
<220> FEATURE:
<223> OTHER INFORMATION: PCR-primer

<400> SEQUENCE: 10
tttgcatgct cattaccgtt cttaacttc                                        29

<210> SEQ ID NO 11

```
<211> LENGTH: 34
<212> TYPE: DNA
<213> ORGANISM: Artificial sequence
<220> FEATURE:
<223> OTHER INFORMATION: PCR-primer

<400> SEQUENCE: 11
ttttaagctt ttatgaagtc catggtaaat tcgt                              34

<210> SEQ ID NO 12
<211> LENGTH: 28
<212> TYPE: DNA
<213> ORGANISM: Artificial sequence
<220> FEATURE:
<223> OTHER INFORMATION: PCR-primer

<400> SEQUENCE: 12
gaattggact tcctggacat tagcttta                                     28

<210> SEQ ID NO 13
<211> LENGTH: 28
<212> TYPE: DNA
<213> ORGANISM: Artificial sequence
<220> FEATURE:
<223> OTHER INFORMATION: PCR-primer

<400> SEQUENCE: 13
cggacattag ctctaatcat aagtggtc                                     28

<210> SEQ ID NO 14
<211> LENGTH: 26
<212> TYPE: DNA
<213> ORGANISM: Artificial sequence
<220> FEATURE:
<223> OTHER INFORMATION: PCR-primer

<400> SEQUENCE: 14
taagtggtcc atcaaagatt tcaatg                                       26

<210> SEQ ID NO 15
<211> LENGTH: 27
<212> TYPE: DNA
<213> ORGANISM: Artificial sequence
<220> FEATURE:
<223> OTHER INFORMATION: PCR-primer

<400> SEQUENCE: 15
caaaaattgg ccgaggctca acaagcc                                      27

<210> SEQ ID NO 16
<211> LENGTH: 25
<212> TYPE: DNA
<213> ORGANISM: Artificial sequence
<220> FEATURE:
<223> OTHER INFORMATION: PCR-primer

<400> SEQUENCE: 16
gttagctcaa ccatccgaat ccttc                                        25

<210> SEQ ID NO 17
<211> LENGTH: 23
<212> TYPE: DNA
<213> ORGANISM: Artificial sequence
<220> FEATURE:
<223> OTHER INFORMATION: PCR-primer

<400> SEQUENCE: 17
```

```
cgaatccttc cagtaccatg cag                                          23

<210> SEQ ID NO 18
<211> LENGTH: 26
<212> TYPE: DNA
<213> ORGANISM: Artificial sequence
<220> FEATURE:
<223> OTHER INFORMATION: PCR-primer

<400> SEQUENCE: 18
cagcgttttc tttcctgtat atgttt                                       26

<210> SEQ ID NO 19
<211> LENGTH: 26
<212> TYPE: DNA
<213> ORGANISM: Artificial sequence
<220> FEATURE:
<223> OTHER INFORMATION: PCR-primer

<400> SEQUENCE: 19
ctactttacc caacggtgct gggttg                                       26

<210> SEQ ID NO 20
<211> LENGTH: 26
<212> TYPE: DNA
<213> ORGANISM: Artificial sequence
<220> FEATURE:
<223> OTHER INFORMATION: PCR-primer

<400> SEQUENCE: 20
caagcgcctc tatgtctgta tcactg                                       26

<210> SEQ ID NO 21
<211> LENGTH: 27
<212> TYPE: DNA
<213> ORGANISM: Artificial sequence
<220> FEATURE:
<223> OTHER INFORMATION: PCR-primer

<400> SEQUENCE: 21
gtatcactgg cctcagctat ggcctac                                      27

<210> SEQ ID NO 22
<211> LENGTH: 24
<212> TYPE: DNA
<213> ORGANISM: Artificial sequence
<220> FEATURE:
<223> OTHER INFORMATION: PCR-primer

<400> SEQUENCE: 22
gaaaaagacc cacataatgg aaca                                         24

<210> SEQ ID NO 23
<211> LENGTH: 27
<212> TYPE: DNA
<213> ORGANISM: Artificial sequence
<220> FEATURE:
<223> OTHER INFORMATION: PCR-primer

<400> SEQUENCE: 23
caattttaag ttcatagatg atttccc                                      27

<210> SEQ ID NO 24
<211> LENGTH: 24
<212> TYPE: DNA
<213> ORGANISM: Artificial sequence
<220> FEATURE:
```

```
<223> OTHER INFORMATION: PCR-primer

<400> SEQUENCE: 24
gaattccaag gcctacaaaa gatc                                          24

<210> SEQ ID NO 25
<211> LENGTH: 25
<212> TYPE: DNA
<213> ORGANISM: Artificial sequence
<220> FEATURE:
<223> OTHER INFORMATION: PCR-primer

<400> SEQUENCE: 25
agagacattt ctcaagagca aattg                                         25

<210> SEQ ID NO 26
<211> LENGTH: 25
<212> TYPE: DNA
<213> ORGANISM: Artificial sequence
<220> FEATURE:
<223> OTHER INFORMATION: PCR-primer

<400> SEQUENCE: 26
gacagcttca acaagaaatt gcaag                                         25

<210> SEQ ID NO 27
<211> LENGTH: 20
<212> TYPE: DNA
<213> ORGANISM: Artificial sequence
<220> FEATURE:
<223> OTHER INFORMATION: PCR-primer

<400> SEQUENCE: 27
cggataacaa tttcacacag                                               20

<210> SEQ ID NO 28
<211> LENGTH: 20
<212> TYPE: DNA
<213> ORGANISM: Artificial sequence
<220> FEATURE:
<223> OTHER INFORMATION: PcR-primer

<400> SEQUENCE: 28
ctgaggtcat tactagatct                                               20

<210> SEQ ID NO 29
<211> LENGTH: 1002
<212> TYPE: DNA
<213> ORGANISM: Paracoccus zeaxanthinifaciens ATCC 21588

<400> SEQUENCE: 29
atgaacgtgc aggaagacgt ccgcaaacca ctggaccggc tggccgaggc gctggcaccc        60
gagatggagg ccgtgaacgc gctgatccgc gaacgcatgg ccagcaggca tgcgccgcgc       120
atccccgagg tgaccgccca cctgatcgag gccggcggca agcgcctgcg cccgatgctg       180
accctggccg cggcgaagct gcttggctat ggcggcccct atcacgtgca tctggccgcg       240
acggtcgaat tcatccacac cgcgaccctg ctgcatgacg acgtggtcga cgaaagccgc       300
cagcgccgcg ggcgtccgac ggcgaacctg ctgtgggaca caagtccag cgtgctggtc        360 ggcgattacc tgttcgcgcg cagcttccag ctgatggtcg aacccggcag catgcgcacg       420
ctcgagatcc tgtcgaacgc cgccgccacc atcgccgagg gcgaggtgct gcagctgacc       480
gcggcgcagg atctggccac gaacgaggac atctatctgc aggtcgtgcg cggcaagacg       540
```

```
gcagcgctgt tctcggccgc gaccgaggtg ggcggcgtca tcgcgggcgt ccccgatgcg    600
caggtccgcg cgctgttcga ttacggcgac gcgcttggca tcgccttcca gatcgtggac    660
gacctgctgg attacggcgg caccgccgag gcgatcggca gaataccgg cgacgatttc     720 cgcgaacgca agctgacgct gccggtgatc aaggccgtgg cccgcgccac ccccgaggaa    780
cgcgccttct ggtcgcgcac catcgagaag ggcgaccaga aggacggcga ccttgaacac    840
gcgctggaac tgctggcccg ccacggcgcg atggccgatg cccgccgcga cgcgctggac    900
tgggcggcca gggcccgcgc ctccctgcag atcctgcccg agcatccgat ccgcgacatg    960
ctgtcggacc tggccgattt cgtggtcgaa cgcatcgcct ga                       1002
```

<210> SEQ ID NO 30
<211> LENGTH: 333
<212> TYPE: PRT
<213> ORGANISM: Paracoccus zeaxanthinifaciens ATCC 21588

<400> SEQUENCE: 30

```
Met Asn Val Gln Glu Asp Val Arg Lys Pro Leu Asp Arg Leu Ala Glu
1               5                   10                  15

Ala Leu Ala Pro Glu Met Glu Ala Val Asn Ala Leu Ile Arg Glu Arg
                20                  25                  30

Met Ala Ser Arg His Ala Pro Arg Ile Pro Glu Val Thr Ala His Leu
            35                  40                  45

Ile Glu Ala Gly Gly Lys Arg Leu Arg Pro Met Leu Thr Leu Ala Ala
        50                  55                  60

Ala Lys Leu Leu Gly Tyr Gly Gly Pro Tyr His Val His Leu Ala Ala
65                  70                  75                  80

Thr Val Glu Phe Ile His Thr Ala Thr Leu Leu His Asp Asp Val Val
                85                  90                  95

Asp Glu Ser Arg Gln Arg Gly Arg Pro Thr Ala Asn Leu Leu Trp
                100                 105                 110

Asp Asn Lys Ser Ser Val Leu Val Gly Asp Tyr Leu Phe Ala Arg Ser
            115                 120                 125

Phe Gln Leu Met Val Glu Pro Gly Ser Met Arg Thr Leu Glu Ile Leu
        130                 135                 140

Ser Asn Ala Ala Ala Thr Ile Ala Glu Gly Glu Val Leu Gln Leu Thr
145                 150                 155                 160

Ala Ala Gln Asp Leu Ala Thr Asn Glu Asp Ile Tyr Leu Gln Val Val
                165                 170                 175

Arg Gly Lys Thr Ala Ala Leu Phe Ser Ala Ala Thr Glu Val Gly Gly
            180                 185                 190

Val Ile Ala Gly Val Pro Asp Ala Gln Val Arg Ala Leu Phe Asp Tyr
        195                 200                 205

Gly Asp Ala Leu Gly Ile Ala Phe Gln Ile Val Asp Asp Leu Leu Asp
    210                 215                 220

Tyr Gly Gly Thr Ala Glu Ala Ile Gly Lys Asn Thr Gly Asp Asp Phe
225                 230                 235                 240

Arg Glu Arg Lys Leu Thr Leu Pro Val Ile Lys Ala Val Ala Arg Ala
                245                 250                 255

Thr Pro Glu Glu Arg Ala Phe Trp Ser Arg Thr Ile Glu Lys Gly Asp
            260                 265                 270

Gln Lys Asp Gly Asp Leu Glu His Ala Leu Glu Leu Leu Ala Arg His
        275                 280                 285

Gly Ala Met Ala Asp Ala Arg Arg Asp Ala Leu Asp Trp Ala Ala Arg
    290                 295                 300
```

```
Ala Arg Ala Ser Leu Gln Ile Leu Pro Glu His Pro Ile Arg Asp Met
305                 310                 315                 320

Leu Ser Asp Leu Ala Asp Phe Val Val Glu Arg Ile Ala
            325                 330
```

<210> SEQ ID NO 31
<211> LENGTH: 395
<212> TYPE: PRT
<213> ORGANISM: mouse

<400> SEQUENCE: 31

```
Met Leu Ser Glu Ala Leu Leu Val Ser Ala Pro Gly Lys Val Ile Leu
1               5                   10                  15

His Gly Glu His Ala Val Val His Gly Lys Val Ala Leu Ala Ala Ala
                20                  25                  30

Leu Asn Leu Arg Thr Phe Leu Leu Arg Pro Gln Ser Asn Gly Lys
            35                  40                  45

Val Ser Val Asn Leu Pro Asn Ile Gly Ile Lys Gln Val Trp Asp Val
    50                  55                  60

Gly Met Leu Gln Arg Leu Asp Thr Ser Phe Leu Glu Gln Gly Asp Val
65                  70                  75                  80

Ser Val Pro Thr Leu Glu Gln Leu Glu Lys Leu Lys Lys Met Gly Asp
                85                  90                  95

Leu Pro Arg Asp Arg Ala Gly Asn Glu Gly Met Ala Leu Leu Ala Phe
            100                 105                 110

Leu Tyr Leu Tyr Leu Ala Ile Cys Arg Lys Gln Arg Thr Leu Pro Ser
        115                 120                 125

Leu Asp Met Val Val Trp Ser Glu Leu Pro Pro Gly Ala Gly Leu Gly
    130                 135                 140

Ser Ser Ala Ala Tyr Ser Val Cys Leu Ala Ala Ala Leu Leu Thr Ala
145                 150                 155                 160

Cys Glu Glu Val Ser Asn Pro Leu Lys Asp Gly Val Ser Val Ser Arg
                165                 170                 175

Trp Pro Glu Glu Asp Leu Lys Ser Ile Asn Lys Trp Ala Phe Glu Gly
            180                 185                 190

Glu Arg Val Ile His Gly Asn Pro Ser Gly Val Asp Asn Ala Val Ser
        195                 200                 205

Thr Trp Gly Gly Ala Leu Arg Phe Gln Gln Gly Thr Met Ser Ser Leu
    210                 215                 220

Lys Ser Leu Pro Ser Leu Gln Ile Leu Leu Thr Asn Thr Lys Val Pro
225                 230                 235                 240

Arg Ser Thr Lys Ala Leu Val Ala Ala Val Arg Ser Arg Leu Thr Lys
                245                 250                 255

Phe Pro Glu Ile Val Ala Pro Leu Leu Thr Ser Ile Asp Ala Ile Ser
            260                 265                 270

Leu Glu Cys Glu Arg Val Leu Gly Glu Met Val Ala Ala Pro Val Pro
        275                 280                 285

Glu Gln Tyr Leu Val Leu Glu Glu Leu Ile Asp Met Asn Gln His His
    290                 295                 300

Leu Asn Ala Leu Gly Val Gly His Asn Ser Leu Asp Gln Leu Cys Gln
305                 310                 315                 320

Val Thr Ala Ala His Gly Leu His Ser Lys Leu Thr Gly Ala Gly Gly
                325                 330                 335

Gly Gly Cys Gly Ile Thr Leu Leu Lys Pro Gly Leu Glu Gln Ala Thr
            340                 345                 350
```

Val Glu Ala Ala Lys Gln Ala Leu Thr Ser Cys Gly Phe Asp Cys Trp
          355                 360                 365

Glu Thr Ser Ile Gly Ala Pro Gly Val Ser Thr His Ser Ala Ala Ala
          370                 375                 380

Val Gly Asp Pro Val Arg Gln Ala Leu Gly Leu
385                 390                 395

<210> SEQ ID NO 32
<211> LENGTH: 395
<212> TYPE: PRT
<213> ORGANISM: Rat

<400> SEQUENCE: 32

Met Leu Ser Glu Val Leu Leu Val Ser Ala Pro Gly Lys Val Ile Leu
1               5                   10                  15

His Gly Glu His Ala Val Val His Gly Lys Val Ala Leu Ala Val Ala
                20                  25                  30

Leu Asn Leu Arg Thr Phe Leu Val Arg Pro Gln Ser Asn Gly Lys
            35                  40                  45

Val Ser Leu Asn Leu Pro Asn Val Gly Ile Lys Gln Val Trp Asp Val
50                  55                  60

Ala Thr Leu Gln Leu Leu Asp Thr Gly Phe Leu Glu Gln Gly Asp Val
65                  70                  75                  80

Pro Ala Pro Thr Leu Glu Gln Leu Gly Lys Leu Lys Lys Val Ala Gly
                85                  90                  95

Leu Pro Arg Asp Cys Val Gly Asn Glu Gly Leu Ser Leu Leu Ala Phe
            100                 105                 110

Leu Tyr Leu Tyr Leu Ala Ile Cys Arg Lys Gln Arg Thr Leu Pro Ser
            115                 120                 125

Leu Asp Ile Met Val Trp Ser Glu Leu Pro Pro Gly Ala Gly Leu Gly
130                 135                 140

Ser Ser Ala Ala Tyr Ser Val Cys Val Ala Ala Ala Leu Leu Thr Ala
145                 150                 155                 160

Cys Glu Glu Val Thr Asn Pro Leu Lys Asp Arg Gly Ser Ile Gly Ser
                165                 170                 175

Trp Pro Glu Glu Asp Leu Lys Ser Ile Asn Lys Trp Ala Tyr Glu Gly
            180                 185                 190

Glu Arg Val Ile His Gly Asn Pro Ser Gly Val Asp Asn Ser Val Ser
            195                 200                 205

Thr Trp Gly Gly Ala Leu Arg Tyr Gln Gln Gly Lys Met Ser Ser Leu
210                 215                 220

Lys Arg Leu Pro Ala Leu Gln Ile Leu Leu Thr Asn Thr Lys Val Pro
225                 230                 235                 240

Arg Ser Thr Lys Ala Leu Val Ala Gly Val Arg Ser Arg Leu Ile Lys
                245                 250                 255

Phe Pro Glu Ile Met Ala Pro Leu Leu Thr Ser Ile Asp Ala Ile Ser
            260                 265                 270

Leu Glu Cys Glu Arg Val Leu Gly Glu Met Ala Ala Pro Val Pro
            275                 280                 285

Glu Gln Tyr Leu Val Leu Glu Glu Leu Met Asp Met Asn Gln His His
            290                 295                 300

Leu Asn Ala Leu Gly Val Gly His Ala Ser Leu Asp Gln Leu Cys Gln
305                 310                 315                 320

Val Thr Ala Ala His Gly Leu His Ser Lys Leu Thr Gly Ala Gly Gly
                325                 330                 335

Gly Gly Cys Gly Ile Thr Leu Leu Lys Pro Gly Leu Glu Arg Ala Lys
            340                 345                 350

Val Glu Ala Ala Lys Gln Ala Leu Thr Gly Cys Gly Phe Asp Cys Trp
        355                 360                 365

Glu Thr Ser Ile Gly Ala Pro Gly Val Ser Met His Ser Ala Thr Ser
370                 375                 380

Ile Glu Asp Pro Val Arg Gln Ala Leu Gly Leu
385                 390                 395

<210> SEQ ID NO 33
<211> LENGTH: 396
<212> TYPE: PRT
<213> ORGANISM: human

<400> SEQUENCE: 33

Met Leu Ser Glu Val Leu Leu Val Ser Ala Pro Gly Lys Val Ile Leu
1               5                   10                  15

His Gly Glu His Ala Val Val His Gly Lys Val Ala Leu Ala Val Ser
            20                  25                  30

Leu Asn Leu Arg Thr Phe Leu Arg Leu Gln Pro His Ser Asn Gly Lys
        35                  40                  45

Val Asp Leu Ser Leu Pro Asn Ile Gly Ile Lys Arg Ala Trp Asp Val
    50                  55                  60

Ala Arg Leu Gln Ser Leu Asp Thr Ser Phe Leu Glu Gln Gly Asp Val
65                  70                  75                  80

Thr Thr Pro Thr Ser Glu Gln Val Glu Lys Leu Lys Glu Val Ala Gly
                85                  90                  95

Leu Pro Asp Asp Cys Ala Val Thr Glu Arg Leu Ala Val Leu Ala Phe
            100                 105                 110

Leu Tyr Leu Tyr Leu Ser Ile Cys Arg Lys Gln Arg Ala Leu Pro Ser
        115                 120                 125

Leu Asp Ile Val Val Trp Ser Glu Leu Pro Pro Gly Ala Gly Leu Gly
    130                 135                 140

Ser Ser Ala Ala Tyr Ser Val Cys Leu Ala Ala Ala Leu Leu Thr Val
145                 150                 155                 160

Cys Glu Glu Ile Pro Asn Pro Leu Lys Asp Gly Asp Cys Val Asn Arg
                165                 170                 175

Trp Thr Lys Glu Asp Leu Glu Leu Ile Asn Lys Trp Ala Phe Gln Gly
            180                 185                 190

Glu Arg Met Ile His Gly Asn Pro Ser Gly Val Asp Asn Ala Val Ser
        195                 200                 205

Thr Trp Gly Gly Ala Leu Arg Tyr His Gln Gly Lys Ile Ser Ser Leu
    210                 215                 220

Lys Arg Ser Pro Ala Leu Gln Ile Leu Leu Thr Asn Thr Lys Val Pro
225                 230                 235                 240

Arg Asn Thr Arg Ala Leu Val Ala Gly Val Arg Asn Arg Leu Leu Lys
                245                 250                 255

Phe Pro Glu Ile Val Ala Pro Leu Leu Thr Ser Ile Asp Ala Ile Ser
            260                 265                 270

Leu Glu Cys Glu Arg Val Leu Gly Glu Met Gly Glu Ala Pro Ala Pro
        275                 280                 285

Glu Gln Tyr Leu Val Leu Glu Glu Leu Ile Asp Met Asn Gln His His
    290                 295                 300

Leu Asn Ala Leu Gly Val Gly His Ala Ser Leu Asp Gln Leu Cys Gln
305                 310                 315                 320

```
Val Thr Arg Ala Arg Gly Leu His Ser Lys Leu Thr Gly Ala Gly Gly
            325                 330                 335

Gly Gly Cys Gly Ile Thr Leu Leu Lys Pro Gly Leu Glu Gln Pro Glu
            340                 345                 350

Val Glu Ala Thr Lys Gln Ala Leu Thr Ser Cys Gly Phe Asp Cys Leu
            355                 360                 365

Glu Thr Ser Ile Gly Ala Pro Gly Val Ser Ile His Ser Ala Thr Ser
    370                 375                 380

Leu Asp Ser Arg Val Gln Gln Ala Leu Asp Gly Leu
385                 390                 395

<210> SEQ ID NO 34
<211> LENGTH: 404
<212> TYPE: PRT
<213> ORGANISM: Schizosaccharomyces pombe

<400> SEQUENCE: 34

Met Ser Lys Ser Leu Ile Val Ser Ser Pro Gly Lys Thr Ile Leu Phe
1               5                   10                  15

Gly Glu His Ala Val Val Tyr Gly Ala Thr Ala Leu Ala Ala Ala Val
            20                  25                  30

Ser Leu Arg Ser Tyr Cys Lys Leu Gln Thr Thr Asn Asn Asn Glu Ile
        35                  40                  45

Val Ile Val Met Ser Asp Ile Gly Thr Glu Arg Arg Trp Asn Leu Gln
    50                  55                  60

Ser Leu Pro Trp Gln His Val Thr Val Glu Asn Val Gln His Pro Ala
65                  70                  75                  80

Ser Ser Pro Asn Leu Asp Leu Leu Gln Gly Leu Gly Glu Leu Leu Lys
                85                  90                  95

Asn Glu Glu Asn Gly Leu Ile His Ser Ala Met Leu Cys Thr Leu Tyr
            100                 105                 110

Leu Phe Thr Ser Leu Ser Ser Pro Ser Gln Gly Cys Thr Leu Thr Ile
        115                 120                 125

Ser Ser Gln Val Pro Leu Gly Ala Gly Leu Gly Ser Ser Ala Thr Ile
    130                 135                 140

Ser Val Val Val Ala Thr Ser Leu Leu Leu Ala Phe Gly Asn Ile Glu
145                 150                 155                 160

Pro Pro Ser Ser Asn Ser Leu Gln Asn Asn Lys Ala Leu Ala Leu Ile
                165                 170                 175

Glu Ala Trp Ser Phe Leu Gly Glu Cys Cys Ile His Gly Thr Pro Ser
            180                 185                 190

Gly Ile Asp Asn Ala Val Ala Thr Asn Gly Gly Leu Ile Ala Phe Arg
        195                 200                 205

Lys Ala Thr Ala His Gln Ser Ala Met Lys Glu Phe Leu Lys Pro Lys
    210                 215                 220

Asp Thr Leu Ser Val Met Ile Thr Asp Thr Lys Gln Pro Lys Ser Thr
225                 230                 235                 240

Lys Lys Leu Val Gln Gly Val Phe Glu Leu Lys Glu Arg Leu Pro Thr
                245                 250                 255

Val Ile Asp Ser Ile Ile Asp Ala Ile Asp Gly Ile Ser Lys Ser Ala
            260                 265                 270

Val Leu Ala Leu Thr Ser Glu Ser Asp Lys Asn Ser Ser Ala Lys Lys
        275                 280                 285

Leu Gly Glu Phe Ile Val Leu Asn Gln Lys Leu Leu Glu Cys Leu Gly
    290                 295                 300
```

```
Val Ser His Tyr Ser Ile Asp Arg Val Leu Gln Ala Thr Lys Ser Ile
305                 310                 315                 320

Gly Trp Thr Lys Leu Thr Gly Ala Gly Gly Gly Cys Thr Ile Thr
            325                 330                 335

Leu Leu Thr Pro Glu Cys Lys Glu Glu Phe Lys Leu Cys Lys Glu
                340                 345                 350

Ser Leu Leu Ala His Lys Asn Ser Ile Tyr Asp Val Gln Leu Gly Gly
            355                 360                 365

Pro Gly Val Ser Val Val Thr Asp Ser Asp Ser Phe Phe Pro Gln Tyr
            370                 375                 380

Glu Ser Asp Phe Asp Phe Lys Lys Leu Asn Leu Leu Ser Lys Phe Asn
385                 390                 395                 400

Lys Tyr Tyr Ile

<210> SEQ ID NO 35
<211> LENGTH: 324
<212> TYPE: PRT
<213> ORGANISM: Aeropyrum pernix

<400> SEQUENCE: 35

Met Arg Arg Ala Ala Arg Ala Ser Ala Pro Gly Lys Val Ile Ile Val
1               5                   10                  15

Gly Glu His Phe Val Val Arg Gly Ser Leu Ala Ile Val Ala Ala Ile
                20                  25                  30

Gly Arg Arg Leu Arg Val Thr Val Arg Ser Gly Gly Lys Gly Ile Val
            35                  40                  45

Leu Glu Ser Ser Met Leu Gly Arg His Ser Ala Pro Leu Pro Gly Gln
50                  55                  60

Gly Ala Ala Ala Lys Val Ser Pro Val Leu Glu Pro Tyr Ile Ala Val
65                  70                  75                  80

Leu Arg Ser Leu Ala Ala Arg Gly Tyr Ser Val Val Pro His Thr Ile
                85                  90                  95

Leu Val Glu Ser Gly Ile Pro Pro Arg Ala Gly Leu Gly Ser Ser Ala
                100                 105                 110

Ala Ser Met Val Ala Tyr Ala Leu Ser Tyr Ser Ala Met His Gly Asp
            115                 120                 125

Pro Leu Ser Ala Glu Asp Leu Tyr Ser Val Ala Met Glu Gly Glu Lys
            130                 135                 140

Ile Ala His Gly Lys Pro Ser Gly Val Asp Val Thr Ile Ala Val Arg
145                 150                 155                 160

Gly Gly Val Leu Ala Tyr Arg Arg Gly Glu Asn Pro Val Asp Ile Arg
                165                 170                 175

Pro Gly Leu Thr Gly Val Thr Leu Leu Val Ala Asp Thr Gly Val Glu
            180                 185                 190

Arg Arg Thr Arg Asp Val Glu His Val Leu Ser Ile Ala Asp Ala
            195                 200                 205

Leu Gly Glu Ala Ser Thr Tyr Ile Tyr Arg Ala Ala Asp Leu Ile Ala
210                 215                 220

Arg Glu Ala Leu His Ala Ile Glu Lys Gly Asp Ala Glu Arg Leu Gly
225                 230                 235                 240

Leu Ile Met Asn Ala Ala Gln Gly Leu Leu Ser Ser Leu Gly Ala Ser
                245                 250                 255

Ser Leu Glu Ile Glu Thr Leu Val Tyr Arg Met Arg Ser Ala Gly Ala
            260                 265                 270
```

```
Leu Gly Ala Lys Leu Thr Gly Ala Gly Trp Gly Gly Cys Val Ile Gly
        275                 280                 285

Leu Phe Lys Glu Gly Glu Val Glu Arg Gly Leu Glu Ser Val Val Glu
290                 295                 300

Ser Ser Ser Gln Ala Phe Thr Ala Ser Ile Ala Glu Glu Gly Ala Arg
305                 310                 315                 320

Leu Glu Glu Phe

<210> SEQ ID NO 36
<211> LENGTH: 335
<212> TYPE: PRT
<213> ORGANISM: Pyrococcus abyssi

<400> SEQUENCE: 36

Met Pro Arg Leu Val Leu Ala Ser Ala Pro Ala Lys Ile Ile Leu Phe
1               5                   10                  15

Gly Glu His Ser Val Val Tyr Gly Lys Pro Ala Ile Ala Ser Ala Ile
                20                  25                  30

Asp Leu Arg Thr Tyr Val Arg Ala Glu Phe Asn Asp Ser Gly Asn Ile
            35                  40                  45

Lys Ile Glu Ala His Asp Ile Lys Thr Pro Gly Leu Ile Val Ser Phe
50                  55                  60

Ser Glu Asp Lys Ile Tyr Phe Glu Thr Asp Tyr Gly Lys Ala Ala Glu
65                  70                  75                  80

Val Leu Ser Tyr Val Arg His Ala Ile Glu Leu Val Leu Glu Glu Ala
                85                  90                  95

Asp Lys Arg Thr Gly Val Ser Val Ser Ile Thr Ser Gln Ile Pro Val
            100                 105                 110

Gly Ala Gly Leu Gly Ser Ser Ala Ala Val Ala Val Ala Thr Ile Gly
        115                 120                 125

Ala Val Ser Lys Leu Leu Asp Leu Glu Leu Ser Lys Glu Glu Ile Ala
130                 135                 140

Lys Met Gly His Lys Val Glu Leu Leu Val Gln Gly Ala Ser Ser Gly
145                 150                 155                 160

Ile Asp Pro Thr Val Ser Ala Ile Gly Gly Phe Leu Tyr Tyr Lys Gln
                165                 170                 175

Gly Glu Phe Glu His Leu Pro Phe Val Glu Leu Pro Ile Val Val Gly
            180                 185                 190

Tyr Thr Gly Ser Ser Gly Ser Thr Lys Glu Leu Val Ala Met Val Arg
        195                 200                 205

Arg Arg Tyr Glu Glu Met Pro Glu Leu Ile Glu Pro Ile Leu Glu Ser
210                 215                 220

Met Gly Lys Leu Val Asp Lys Ala Lys Glu Val Ile Ile Ser Lys Leu
225                 230                 235                 240

Asp Glu Glu Glu Lys Phe Leu Lys Leu Gly Glu Leu Met Asn Ile Asn
                245                 250                 255

His Gly Leu Leu Asp Ala Leu Gly Val Ser Thr Lys Lys Leu Ser Glu
            260                 265                 270

Leu Val Tyr Ala Ala Arg Thr Ala Gly Ala Ile Gly Ala Lys Leu Thr
        275                 280                 285

Gly Ala Gly Gly Gly Gly Cys Met Tyr Ala Leu Ala Pro Gly Lys Gln
290                 295                 300

Arg Glu Val Ala Thr Ala Ile Lys Ile Ala Gly Gly Thr Pro Met Ile
305                 310                 315                 320

Thr Arg Ile Ser Lys Glu Gly Leu Arg Ile Glu Glu Val Arg Glu
```

<210> SEQ ID NO 37
<211> LENGTH: 335
<212> TYPE: PRT
<213> ORGANISM: Pyrococcus horikoshii

<400> SEQUENCE: 37

Met Val Lys Tyr Val Leu Ala Ser Ala Pro Ala Lys Val Ile Leu Phe
1               5                   10                  15

Gly Glu His Ser Val Val Tyr Gly Lys Pro Ala Ile Ala Ser Ala Ile
            20                  25                  30

Glu Leu Arg Thr Tyr Val Arg Ala Gln Phe Asn Asp Ser Gly Asn Ile
        35                  40                  45

Lys Ile Glu Ala His Asp Ile Lys Thr Pro Gly Leu Ile Val Ser Phe
    50                  55                  60

Ser Glu Asp Lys Ile Tyr Phe Glu Thr Asp Tyr Gly Lys Ala Ala Glu
65                  70                  75                  80

Val Leu Ser Tyr Val Arg Tyr Ala Ile Glu Leu Ala Leu Glu Glu Ser
                85                  90                  95

Asp Lys Arg Val Gly Ile Asp Val Ser Ile Thr Ser Gln Ile Pro Val
            100                 105                 110

Gly Ala Gly Leu Gly Ser Ser Ala Ala Val Ala Val Ala Thr Ile Gly
        115                 120                 125

Ala Val Ser Arg Leu Leu Gly Leu Glu Leu Ser Lys Glu Glu Ile Ala
    130                 135                 140

Lys Leu Gly His Lys Val Glu Leu Leu Val Gln Gly Ala Ser Ser Gly
145                 150                 155                 160

Ile Asp Pro Thr Val Ser Ala Val Gly Gly Phe Leu Tyr Tyr Lys Gln
                165                 170                 175

Gly Lys Phe Glu Pro Leu Pro Phe Met Glu Leu Pro Ile Val Val Gly
            180                 185                 190

Tyr Thr Gly Ser Thr Gly Ser Thr Lys Glu Leu Val Ala Met Val Arg
        195                 200                 205

Lys Arg Tyr Glu Glu Met Pro Glu Leu Val Glu Pro Ile Leu Glu Ala
    210                 215                 220

Met Gly Lys Leu Val Asp Lys Ala Lys Glu Ile Ile Leu Ser Lys Leu
225                 230                 235                 240

Asp Glu Glu Glu Lys Leu Thr Lys Leu Gly Glu Leu Met Asn Ile Asn
                245                 250                 255

His Gly Leu Leu Asp Ala Leu Gly Val Ser Thr Lys Lys Leu Gly Glu
            260                 265                 270

Leu Val Tyr Ala Ala Arg Thr Ala Gly Ala Ile Gly Ala Lys Leu Thr
        275                 280                 285

Gly Ala Gly Gly Gly Gly Cys Met Tyr Ala Leu Ala Pro Gly Arg Gln
    290                 295                 300

Arg Glu Val Ala Thr Ala Ile Lys Ile Ala Gly Gly Ile Pro Met Ile
305                 310                 315                 320

Thr Arg Val Ser Arg Glu Gly Leu Arg Ile Glu Glu Val Ser Arg
                325                 330                 335

<210> SEQ ID NO 38
<211> LENGTH: 334
<212> TYPE: PRT
<213> ORGANISM: Pyrococcus furiosus

<400> SEQUENCE: 38

-continued

```
Met Lys Val Ile Ala Ser Ala Pro Ala Lys Val Ile Leu Phe Gly Glu
1               5                   10                  15

His Ser Val Val Tyr Gly Lys Pro Ala Ile Ala Ala Ile Asp Leu
            20                  25                  30

Arg Thr Phe Val Glu Ala Glu Leu Ile Arg Glu Lys Lys Ile Arg Ile
            35                  40                  45

Glu Ala His Asp Ile Lys Val Pro Gly Leu Thr Val Ser Phe Ser Glu
50                  55                  60

Asn Glu Ile Tyr Phe Glu Thr Asp Tyr Gly Lys Ala Ala Glu Val Leu
65                  70                  75                  80

Ser Tyr Val Arg Glu Ala Ile Asn Leu Val Leu Glu Glu Ala Asp Lys
                85                  90                  95

Lys Asn Val Gly Ile Lys Val Ser Ile Thr Ser Gln Ile Pro Val Gly
            100                 105                 110

Ala Gly Leu Gly Ser Ser Ala Ala Val Ala Val Ala Thr Ile Gly Ala
            115                 120                 125

Val Ser Lys Leu Leu Gly Leu Glu Leu Ser Lys Glu Glu Ile Ala Lys
130                 135                 140

Met Gly His Lys Thr Glu Leu Leu Val Gln Gly Ala Ser Ser Gly Ile
145                 150                 155                 160

Asp Pro Thr Val Ser Ala Ile Gly Gly Phe Ile Phe Tyr Glu Lys Gly
                165                 170                 175

Lys Phe Glu His Leu Pro Phe Met Glu Leu Pro Ile Val Val Gly Tyr
            180                 185                 190

Thr Gly Ser Ser Gly Pro Thr Lys Glu Leu Val Ala Met Val Arg Lys
        195                 200                 205

Arg Tyr Glu Glu Met Pro Glu Leu Ile Val Pro Ile Leu Glu Ala Met
    210                 215                 220

Gly Lys Val Val Glu Lys Ala Lys Asp Val Ile Leu Ser Asn Val Asp
225                 230                 235                 240

Lys Glu Glu Lys Phe Glu Arg Leu Gly Val Leu Met Asn Ile Asn His
                245                 250                 255

Gly Leu Leu Asp Ala Leu Gly Val Ser Thr Lys Lys Leu Ser Glu Leu
            260                 265                 270

Val Tyr Ala Ala Arg Val Ala Gly Ala Leu Gly Ala Lys Ile Thr Gly
        275                 280                 285

Ala Gly Gly Gly Gly Cys Met Tyr Ala Leu Ala Pro Asn Lys Gln Arg
    290                 295                 300

Glu Val Ala Thr Ala Ile Arg Ile Ala Gly Gly Thr Pro Met Ile Thr
305                 310                 315                 320

Glu Ile Ser Arg Glu Gly Leu Lys Ile Glu Glu Val Ile Lys
                325                 330
```

<210> SEQ ID NO 39
<211> LENGTH: 303
<212> TYPE: PRT
<213> ORGANISM: Methanobacterium thermoautotrophicum

<400> SEQUENCE: 39

```
Met Lys Ser Ser Ala Ser Ala Pro Ala Lys Ala Ile Leu Phe Gly Glu
1               5                   10                  15

His Ala Val Val Tyr Ser Lys Pro Ala Ile Ala Ala Ile Asp Arg
            20                  25                  30

Arg Val Thr Val Thr Val Ser Glu Ser Ser Thr His Val Thr Ile
        35                  40                  45
```

Pro Ser Leu Gly Ile Arg His Ser Ser Glu Arg Pro Ser Gly Gly Ile
    50                  55                  60

Leu Asp Tyr Ile Gly Arg Cys Leu Glu Leu Tyr His Asp Ala Ser Pro
65                  70                  75                  80

Leu Asp Ile Arg Val Glu Met Glu Ile Pro Ala Gly Ser Gly Leu Gly
                85                  90                  95

Ser Ser Ala Ala Leu Thr Val Ala Leu Ile Gly Ala Leu Asp Arg Tyr
            100                 105                 110

His Gly Arg Asp His Gly Pro Gly Glu Thr Ala Ala Arg Ala His Arg
        115                 120                 125

Val Glu Val Asp Val Gln Gly Ala Ala Ser Pro Leu Asp Thr Ala Ile
    130                 135                 140

Ser Thr Tyr Gly Gly Leu Val Tyr Leu Asp Ser Gln Arg Arg Val Arg
145                 150                 155                 160

Gln Phe Glu Ala Asp Leu Gly Asp Leu Val Ile Ala His Leu Asp Tyr
                165                 170                 175

Ser Gly Glu Thr Ala Arg Met Val Ala Gly Val Ala Glu Arg Phe Arg
            180                 185                 190

Arg Phe Pro Asp Ile Met Gly Arg Ile Met Asp Thr Val Glu Ser Ile
        195                 200                 205

Thr Asn Thr Ala Tyr Arg Glu Leu Leu Arg Asn Asn Thr Glu Pro Leu
    210                 215                 220

Gly Glu Leu Met Asn Leu Asn Gln Gly Leu Leu Asp Ser Met Gly Val
225                 230                 235                 240

Ser Thr Arg Glu Leu Ser Met Met Val Tyr Glu Ala Arg Asn Ala Gly
                245                 250                 255

Ala Ala Gly Ser Lys Ile Thr Gly Ala Gly Gly Gly Ser Ile Ile
            260                 265                 270

Ala His Cys Pro Gly Cys Val Asp Asp Val Val Thr Ala Leu Asn Arg
        275                 280                 285

Asn Trp Lys Ala Met Arg Ala Glu Phe Ser Val Lys Gly Leu Ile
    290                 295                 300

<210> SEQ ID NO 40
<211> LENGTH: 284
<212> TYPE: PRT
<213> ORGANISM: Archaeoglobus fulgidus

<400> SEQUENCE: 40

Met Ile Ala Ser Ala Pro Gly Lys Ile Ile Leu Phe Gly Glu His Ala
1               5                   10                  15

Val Val Tyr Gly Arg His Ala Val Ser Ala Ile Asn Leu Arg Cys
            20                  25                  30

Arg Val Ser Val Arg Lys Ser Asp Arg Phe Leu Ile Arg Ser Ser Leu
        35                  40                  45

Gly Glu Ser Gly Leu Asp Tyr Gln Arg His Pro Tyr Val Val Gln Ala
    50                  55                  60

Val Lys Arg Phe Gly Glu Leu Arg Asn Ile Pro Gly Ala Glu Ile Glu
65                  70                  75                  80

Ile Glu Ser Glu Ile Pro Ile Gly Ser Gly Leu Gly Ser Ser Ala Ala
                85                  90                  95

Val Ile Val Ala Thr Ile Ala Ala Leu Asn Ala Glu Phe Asp Gly Asp
            100                 105                 110

Met Asp Lys Glu Ala Ile Phe Gln Met Ala Lys Gln Val Glu Ile Asp
        115                 120                 125

```
Val Gln Gly Arg Ala Ser Gly Ile Asp Pro Phe Ile Ser Thr Phe Gly
    130                 135                 140

Gly Ser Trp Leu Phe Pro Glu Arg Arg Lys Val Glu Met Pro Phe Lys
145                 150                 155                 160

Phe Phe Val Ile Asn Phe Gly Ser Arg Ser Thr Ala Glu Met Val Ala
                165                 170                 175

Lys Val Ala Glu Leu Arg Glu Arg His Pro Glu Val Val Asp Lys Ile
            180                 185                 190

Phe Asp Ala Ile Asp Ala Ile Ser Leu Glu Ala Ser Asp Val Gly Ser
        195                 200                 205

Ala Glu Arg Leu Glu Glu Leu Ile Ala Ile Asn Gln Ser Leu Leu Arg
    210                 215                 220

Ala Ile Gly Val Ser Asn Pro Glu Ile Asp Arg Thr Ile Ala Glu Leu
225                 230                 235                 240

Glu Arg Met Gly Leu Asn Ala Lys Ile Thr Gly Ala Gly Gly Gly
                245                 250                 255

Cys Ile Phe Gly Leu Phe Lys Gly Glu Lys Pro Lys Gly Ser Phe Ile
                260                 265                 270

Val Glu Pro Glu Lys Glu Gly Val Arg Ile Glu Glu
            275                 280

<210> SEQ ID NO 41
<211> LENGTH: 312
<212> TYPE: PRT
<213> ORGANISM: Methanococcus jannaschii

<400> SEQUENCE: 41

Met Ile Ile Glu Thr Pro Ser Lys Val Ile Leu Phe Gly Glu His Ala
1               5                   10                  15

Val Val Tyr Gly Tyr Arg Ala Ile Ser Met Ala Ile Asp Leu Thr Ser
            20                  25                  30

Thr Ile Glu Ile Lys Glu Thr Gln Glu Asp Glu Ile Ile Leu Asn Leu
        35                  40                  45

Asn Asp Leu Asn Lys Ser Leu Gly Leu Asn Leu Asn Glu Ile Lys Asn
    50                  55                  60

Ile Asn Pro Asn Asn Phe Gly Asp Phe Lys Tyr Cys Leu Cys Ala Ile
65                  70                  75                  80

Lys Asn Thr Leu Asp Tyr Leu Asn Ile Glu Pro Lys Thr Gly Phe Lys
                85                  90                  95

Ile Asn Ile Ser Ser Lys Ile Pro Ile Ser Cys Gly Leu Gly Ser Ser
            100                 105                 110

Ala Ser Ile Thr Ile Gly Thr Ile Lys Ala Val Ser Gly Phe Tyr Asn
        115                 120                 125

Lys Glu Leu Lys Asp Asp Glu Ile Ala Lys Leu Gly Tyr Met Val Glu
    130                 135                 140

Lys Glu Ile Gln Gly Lys Ala Ser Ile Thr Asp Thr Ser Thr Ile Thr
145                 150                 155                 160

Tyr Lys Gly Ile Leu Glu Ile Lys Asn Asn Lys Phe Arg Lys Ile Lys
                165                 170                 175

Gly Glu Phe Glu Glu Phe Leu Lys Asn Cys Lys Phe Leu Ile Val Tyr
            180                 185                 190

Ala Glu Lys Arg Lys Lys Thr Ala Glu Leu Val Asn Glu Val Ala
        195                 200                 205

Lys Ile Glu Asn Lys Asp Glu Ile Phe Lys Glu Ile Asp Lys Val Ile
    210                 215                 220
```

```
Asp Glu Ala Leu Lys Ile Lys Asn Lys Glu Asp Phe Gly Lys Leu Met
225                 230                 235                 240

Thr Lys Asn His Glu Leu Leu Lys Lys Leu Asn Ile Ser Thr Pro Lys
            245                 250                 255

Leu Asp Arg Ile Val Asp Ile Gly Asn Arg Phe Gly Phe Gly Ala Lys
            260                 265                 270

Leu Thr Gly Ala Gly Gly Gly Cys Val Ile Ile Leu Val Asn Glu
        275             280                 285

Glu Lys Glu Lys Glu Leu Leu Lys Glu Leu Asn Lys Glu Asp Val Arg
    290                 295                 300

Ile Phe Asn Cys Arg Met Met Asn
305             310
```